(12) United States Patent
Garcia et al.

(10) Patent No.: US 8,389,547 B2
(45) Date of Patent: *Mar. 5, 2013

(54) PIPERIDINES AND RELATED COMPOUNDS FOR THE TREATMENT OF ALZHEIMER'S DISEASE

(76) Inventors: Yudith Garcia, Brookline, MA (US); Joanne Clare Hannam, Canterbury (GB); Timothy Harrison, Belfast (IE); Christopher L. Hamblett, Boston, MA (US); Jed L. Hubbs, Cambridge, MA (US); Janusz Josef Kulagowski, Sawbridgeworth (GB); Andrew Madin, Cambridge (GB); Mark Peter Ridgill, Dover (GB); Eileen Seward, Bishop Stortford (GB)

( * ) Notice: Subject to any disclaimer, the term of this patent is extended or adjusted under 35 U.S.C. 154(b) by 781 days.

This patent is subject to a terminal disclaimer.

(21) Appl. No.: 12/298,394

(22) PCT Filed: Apr. 25, 2007

(86) PCT No.: PCT/GB2007/050213
§ 371 (c)(1),
(2), (4) Date: Oct. 2, 2009

(87) PCT Pub. No.: WO2007/125364
PCT Pub. Date: Nov. 8, 2007

(65) Prior Publication Data
US 2010/0048623 A1    Feb. 25, 2010

Related U.S. Application Data

(60) Provisional application No. 60/795,331, filed on Apr. 26, 2006.

(51) Int. Cl.
*A61K 31/445* (2006.01)
*C07D 211/34* (2006.01)
(52) U.S. Cl. ......... 514/317; 514/326; 546/210; 546/237
(58) Field of Classification Search .............. 514/317, 514/326; 546/210, 237
See application file for complete search history.

(56) References Cited

U.S. PATENT DOCUMENTS 7,638,629 B2 * 12/2009 Hannam et al. ............... 546/124
2009/0239905 A1 * 9/2009 Hannam et al. ............... 514/314
2010/0093665 A1 * 4/2010 Munoz et al. ................... 514/63

FOREIGN PATENT DOCUMENTS

| EP | 0528495 | 2/1993 |
| WO | WO 99/36424 | 7/1999 |
| WO | WO 2006/004880 | 1/2006 |
| WO | W02006043064 | 4/2006 |

OTHER PUBLICATIONS

Braga et al. "Making crystals from . . . " J. Roy. Soc. Chem. Chem. Commun. p. 3635-3645 (2005).*
Esler et al. "Transition state . . . " Nature Cell Biol. v.2, p. 428-434 (2000).*
Garofalo "Patents targeting . . . " Exp. Opinion Ther. Patents 18(7) 693-703 (2008).*
Heike et al. "Design synthesis . . . " J. Med. Chem. v.53, p. 4691-4700 (2010).*
Szekely et al. "Prevention of Alzheimer . . . " Int. Rev. Psych. v. 19(6) p. 693-706 (2007).*
Communication pursuant to Article 94(3) EPC dated Mar. 11, 2010 for EP Application No. 07 733 634.5.

* cited by examiner

*Primary Examiner* — Celia Chang
(74) *Attorney, Agent, or Firm* — Susan L. Hess; Gerard M. Devlin; Raynard Yuro

(57) ABSTRACT

Compounds of formula (I) are modulators of gamma-secretase, and hence are useful in treatment of Alzheimer's disease.

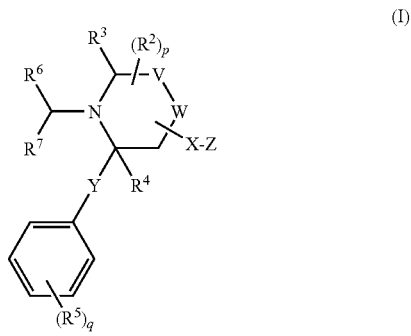

11 Claims, No Drawings

PIPERIDINES AND RELATED COMPOUNDS FOR THE TREATMENT OF ALZHEIMER'S DISEASE

RELATED APPLICATION DATA

This is a National filing under 35 U.S.C. 371 of PCT/GB2007/050213, filed Apr. 25, 2007, which claims priority to U.S. Provisional Application No. 60/795,331, filed Apr. 26, 2006.

This invention relates to compounds for use in therapeutic treatment of the human body. In particular, it provides carboxy-functional 1,2-disubstituted piperidines and related compounds useful for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, *PNAS*, 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral hemorrhage with amyloidosis, Dutch-type (HCHWA-D), multi-infarct dementia, dementia pugilistica and Down syndrome.

Various interventions in the plaque-forming process have been proposed as therapeutic treatments for AD (see, for example, Hardy and Selkoe, *Science*, 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Phiel et al, *Nature*, 423 (2003), 435-9).

Other proposed methods of treatment include administering a compound which blocks the aggregation of Aβ, and administering an antibody which selectively binds to Aβ.

Another proposed treatment is that of modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and US 2002/0128319 and Weggen et al *Nature*, 414 (2001) 212-16; Morihara et al, *J. Neurochem.*, 83 (2002), 1009-12; and Takahashi et al, *J. Biol. Chem.*, 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce intracerebral Aβ deposition in animal models (WO 02/092072; Jantzen et al, *J. Neuroscience*, 22 (2002), 226-54). US 2002/0015941 teaches that agents which potentiate capacitative calcium entry activity can lower Aβ(1-42).

It has now been found that certain carboxy-functional 1,2-disubstituted piperidines and related compounds have the desirable property of selectively inhibiting production of Aβ(1-42) with a high degree of potency and/or selectivity.

According to the present invention there is provided a compound of formula I:

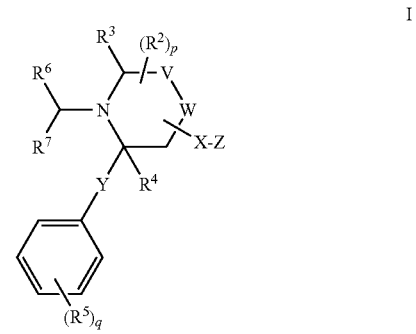

or a pharmaceutically acceptable salt or hydrate thereof, wherein:

p is 0 or 1;

q is 0, 1, 2 or 3;

V represents a bond or a carbon atom whose remaining valencies are satisfied via bonding to H, $R^2$ or X-Z or to any combination thereof;

W represents a nitrogen atom or a carbon atom whose remaining valencies are satisfied via bonding to H, $R^2$ or X-Z or to any combination thereof, provided that when W represents a nitrogen atom, V represents a carbon atom and the moiety X-Z is attached to W;

X represents a bond or $C(R^1)_2$ or $CH_2C(R^1)_2$, provided that when W represents N, X does not represent a bond;

Y represents a bond or $CH_2$ or $CH_2CH_2$;

Z represents $CO_2H$ or a tetrazole ring;

each $R^1$ independently represents H or a non-aromatic hydrocarbon group of up to 6 carbon atoms; or the two $R^1$ groups complete a $C_{3-6}$alicyclic group;

$R^2$ represents a non-aromatic hydrocarbon group of up to 6 carbon atoms;

$R^3$ and $R^4$ each represents H, or when V and W each represents a carbon atom, $R^3$ and $R^4$ may together represent a $CH_2CH_2$ bridge;

each $R^5$ independently represents halogen, $C_{1-6}$alkyl bearing 0-3 fluorine substituents, $C_{1-6}$alkoxy bearing 0-3 fluorine substituents, $C_{2-6}$alkenyl or $Si(C_{1-4}alkyl)_3$; and $R^6$ and $R^7$ independently represent linear or branched hydrocarbon groups each containing up to 10 carbon atoms optionally bearing a substituent selected from perfluoro$C_{1-4}$ alkyl, $C_{3-6}$alicyclic, hydroxy$C_{3-6}$alicyclic, OH, $C_{1-4}$alkoxy, phenyl or benzyloxy, where said $C_{1-4}$alkoxy, phenyl and benzyloxy substituents themselves bear 0-3 substituents selected from halogen, $C_{1-4}$alkyl, $C_{1-4}$alkoxy and. perfluoro$C_{1-4}$alkyl.

In a particular embodiment, each $R^5$ independently represents halogen, $C_{1-6}$alkyl bearing 0-3 fluorine substituents, $C_{1-6}$alkoxy bearing 0-3 fluorine substituents, or $C_{2-6}$alkenyl, and all other variables are as defined previously.

Where a variable occurs more than once in formula I, the identity taken by said variable at any particular occurrence is independent of the identity taken at any other occurrence.

As used herein, the expression "hydrocarbon group" refers to groups consisting solely of carbon and hydrogen atoms. Unless indicated otherwise, such groups may comprise linear, branched or cyclic structures, singly or in any combination consistent with the indicated maximum number of carbon atoms, and may be saturated or unsaturated.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner.

The expression "perfluoro$C_{1-4}$alkyl" refers to linear or branched alkyl groups of up to 4 carbon atoms in which all the hydrogen atoms are replaced by fluorine atoms.

The expression "$C_{3-6}$alicyclic" refers to cyclic non-aromatic hydrocarbon groups containing from 3 to 6 ring carbon atoms. Examples include cyclopropyl, cyclobutyl, cyclopentenyl, cyclopentyl and cyclohexyl.

The term "halogen" as used herein includes fluorine, chlorine, bromine and iodine, of which fluorine and chlorine are preferred unless otherwise indicated.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, a pharmaceutically acceptable salt may be formed by neutralisation of the carboxylic acid group with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be understood that all the isomeric forms encompassed by formula I, both optical and geometrical, fall within the scope of the invention, singly or as mixtures in any proportion. Thus the moieties:

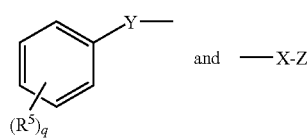

may be in a cis- or trans-configuration with respect to the ring completed by V-W. Furthermore, a given compound in the cis- or trans-configuration has two enantiomeric forms, both of which are within the scope of the invention, whether as single homochiral compounds or as racemic mixtures in any proportion. For the avoidance of any doubt, structural formulae such as (A) and (B):

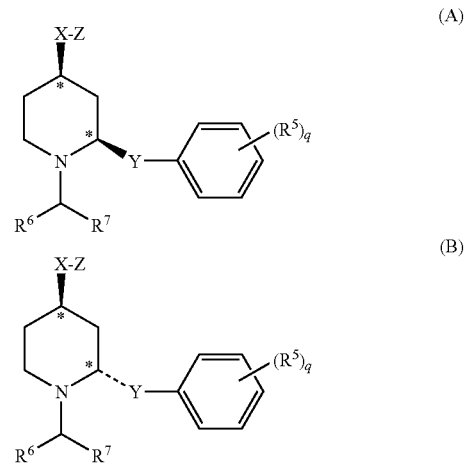

as used herein shall be taken to be definitive of the relative configurations of the carbon atoms marked with asterisks, but not their absolute configurations, unless expressly stated otherwise.

In formula I, V represents a bond or a carbon atom and W represents a nitrogen atom or a carbon atom, with the proviso that when W represents a nitrogen atom, V cannot be a bond and the moiety X-Z must be attached to W. Formula I therefore encompasses pyrrolidine, piperidine and piperazine derivatives, depending on the identities of V and W. In preferred embodiments, V represents a carbon atom, and hence completes a piperidine or piperazine ring. Most preferably, V and W both represent carbon atoms, and hence complete a piperidine ring. When one or both of V and W represents a carbon atom, the remaining valencies of said carbon atom(s) are satisfied via bonding to H, $R^2$ or X-Z, or to any combination thereof.

The moiety X-Z may be attached at any available ring position, including ring positions represented by V and W, but when W represents a nitrogen atom, X-Z must be attached to W. Preferably, X-Z is not attached at either of the positions adjacent to the nitrogen atom which is bonded to the moiety —CHR$^6$R$^7$. Thus, in the case of the preferred piperidine rings, X-Z is typically attached at the 3-, 4- or 5-position, preferably the 3- or 4-position, and most preferably at the 4-position. For the avoidance of doubt, the nitrogen atom of the piperidine ring shall be taken as the 1-position, and the carbon atom bonded to Y and $R^4$ as the 2-position.

Z represents $CO_2H$ or a tetrazole ring, in particular, Z represents $CO_2H$ or 1,2,3,4-tetrazol-5-yl, but preferably represents $CO_2H$.

The group X represents a bond, $C(R^1)_2$ or $CH_2C(R^1)_2$, where each $R^1$ independently represents H or a non-aromatic hydrocarbon group of up to 6 carbon atoms; or the two $R^1$ groups complete a $C_{3-6}$alicyclic group (such as cyclopropyl, cyclobutyl, cyclopentenyl or cyclopentyl). In one embodiment, one $R^1$ group is H and the other is H or $C_{1-6}$alkyl such as methyl, ethyl, propyl or butyl. In another embodiment, both $R^1$ groups represent methyl or together complete an alicyclic group. Particular identities for X include a bond, $CH_2$, $CH(CH_3)$, $C(CH_3)_2$, $CH_2CH_2$, cyclopentan-1,1-diyl and cyclopent-3-en-1,1-diyl, with the proviso that when W represents a nitrogen atom, X cannot be a bond. Preferably, X represents a bond or $CH_2$, and most preferably X represents $CH_2$.

Y represents a bond, $CH_2$ or $CH_2CH_2$, preferably a bond or $CH_2$, and most preferably a bond.

The group $R^2$ (when present) may be attached at any available position on the ring, including a carbon atom represented by V or W and including a carbon atom to which the moiety X-Z is attached. In one particular embodiment, p is 0 and $R^2$ is absent. In another particular embodiment, p is 1, V and W complete a piperidine ring and $R^2$ and the moiety X-Z are both attached at the 4-position thereof. In another particular embodiment, p is 1, V and W complete a piperidine ring, $R^2$ is attached at the 3-position and the moiety X-Z is attached at the 4-position. In another particular embodiment, p is 1, $R^3$ is H, V and W complete a piperidine ring, $R^2$ is attached at the 6-position and the moiety X-Z is attached at the 4-position. Typical identities for $R^2$ include $C_{1-6}$alkyl, such as methyl, ethyl or n-propyl, and $C_{2-6}$alkenyl, such as allyl.

$R^3$ and $R^4$ each represent H, or when V and W each represents a carbon atom, $R^3$ and $R^4$ may together represent —$CH_2CH_2$—, thereby completing a bridged bicyclic structure. When $R^3$ and $R^4$ together represent —$CH_2CH_2$—, p is preferably 0, and Y is preferably a bond. In a particular embodiment, $R^3$ and $R^4$ both represent H.

In formula I, q is preferably 1 or 2, most preferably 1. Each $R^5$ independently represents halogen (especially F), $C_{1-6}$alkyl bearing 0-3 fluorine substituents, $C_{1-6}$alkoxy bearing 0-3 fluorine substituents, $C_{2-6}$alkenyl or $Si(C_{1-4}alkyl)_3$. When one $R^5$ is present, it is very suitably (but not necessarily) attached in the 4-position. Typical identities for $(R^5)_q$ include 2-$CF_3$, 3-$CF_3$, 4-$CF_3$, 2,4-di($CF_3$), 2-F-4-$CF_3$, 4-$OCF_3$, 4-allyl, 4-n-propyl, 4-isopropyl and 4-tert-butyl. In one embodiment, $(R^5)_q$ represents 4-$CF_3$ or 4-n-propyl, in particular 4-$CF_3$. In a further embodiment $(R^5)_q$ represents 4-$SiMe_3$.

$R^6$ and $R^7$ independently represent linear or branched (i.e. non-cyclic) hydrocarbon groups containing up to 10 carbon atoms optionally bearing a substituent as defined previously. Said hydrocarbon groups may be fully saturated or may comprise one or more double or triple bonds or combinations thereof. Thus, in one embodiment $R^6$ and $R^7$ are independently selected from $C_{1-10}$alkyl, $C_{2-10}$alkenyl, $C_{2-10}$alkynyl and $C_{2-10}$alkenylalkynyl groups which optionally bear a substituent as defined previously. Typically, hydrocarbon groups represented by $R^6$ and $R^7$ contain up to 8 carbon atoms, e.g. up to 6 carbon atoms. However, if neither of $R^6$ and $R^7$ bears a substituent, at least one of the hydrocarbon groups represented by $R^6$ and $R^7$ preferably comprises 4 or more carbon atoms.

Examples of unsubstituted hydrocarbon groups represented by $R^6$ and/or $R^7$ include methyl, ethyl, n-propyl, isopropyl, n-butyl, isobutyl, t-butyl, 3-methylbutyl, 2-ethylbutyl, 4-methylpentyl, 3,3-dimethylbutyl, 3-methyl-1-butenyl, 3-methyl-3-butenyl, 3-methyl-3-butene-1-ynyl, 4-methyl-1-pentynyl and 3,3-dimethyl-1-butynyl.

In a particular embodiment, one or both of $R^6$ and $R^7$ bears a substituent selected from perfluoro$C_{1-4}$alkyl (such as $CF_3$ or $C_2F_5$), $C_{3-6}$alicyclic (such as cyclopropyl, cyclohexyl or cyclohexenyl), hydroxy$C_{3-6}$alicyclic (such as 1-hydroxycyclopentyl or 1-hydroxycyclohexyl), OH, $C_{1-4}$alkoxy (such as methoxy or isopropoxy), phenyl or benzyloxy, where said $C_{1-4}$alkoxy, phenyl and benzyloxy substituents themselves optionally bear up to 3 substituents selected from halogen, $C_{1-4}$alkyl, $C_{1-4}$alkoxy and perfluoro$C_{1-4}$alkyl (e.g. difluoromethoxy, 3-fluorophenyl, 3,5-difluorophenyl, 2,4-difluorophenyl, 3-methylphenyl, 4-t-butylphenyl, 3-(trifluoromethyl)phenyl and 4-(trifluoromethyl)phenyl). When $R^6$ or $R^7$ bears a substituent, its total number of carbon atoms (i.e. including those contributed by the substituent) is typically not more than 14, and preferably not more than 12.

Examples of substituted hydrocarbon groups represented by $R^6$ and/or $R^7$ include 2,2,2-trifluoroethyl, 3,3,3-trifluoropropyl, 4,4,4-trifluorobutyl, 2-phenylethyl, 3-methoxyprop-1-ynyl, cyclohexylethynyl, 1-methyl-3,3,3-trifluoropropyl, 2,2,3,3,3-pentafluoropropyl, hydroxymethyl, isopropoxymethyl, difluoromethoxymethyl, 4-benzyloxy-3-methyl-1-butynyl, 4-hydroxy-3-methyl-1-butynyl, 4-benzyloxy-3-methylbutyl, 4-hydroxy-3-methylbutyl, 2-cyclopropylethyl, 2-cyclohexylethyl, 2-(cyclohexen-1-yl)ethyl, 2-(1-hydroxycyclopentyl)ethyl, 2-(1-hydroxycyclohexyl)ethyl, 2-(3-fluorophenyl)ethyl, 2-(3,5-difluorophenyl)ethyl, 2-(2,4-difluorophenyl)ethyl, 2-(3-methylphenyl)ethyl, 2-(4-t-butylphenyl)ethyl, 2-[3-(trifluoromethyl)phenyl]ethyl and 2-[4-(trifluoromethyl)phenyl]ethyl.

A first subset of the compounds according to the invention consists of the compounds of formula II:

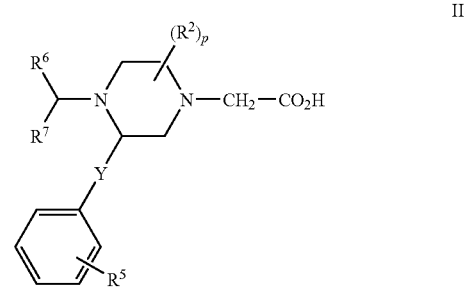

and the pharmaceutically acceptable salts and hydrates thereof;
wherein p, $R^2$, $R^5$, $R^6$ and $R^7$ have the same definitions and preferred identities as before.

In a particular embodiment of this subset, p is 0 and Y is a bond.

A second subset of the compounds according to the invention consists of the compounds of formula III:

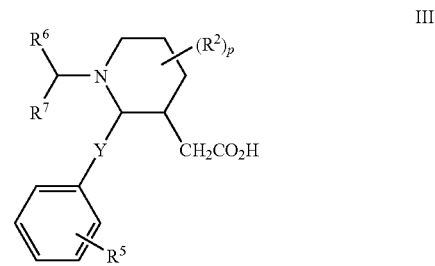

and the pharmaceutically acceptable salts and hydrates thereof;
wherein p, $R^2$, Y, $R^5$, $R^6$ and $R^7$ have the same definitions and preferred identities as before.

Within this subset, Y is preferably a bond, and p is preferably 0.

A third subset of the compounds according to the invention consists of the compounds of formula IV:

IV

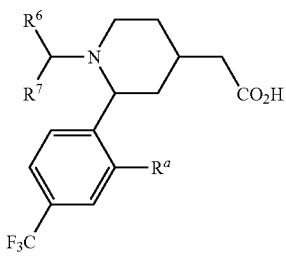

and the pharmaceutically acceptable salts and hydrates thereof, wherein:

$R^a$ represents H, halogen or $CF_3$;

and $R^6$ and $R^7$ have the same definitions and preferred identities as before.

The substituted phenyl group attached to the 2-position of the piperidine ring and the $CH_2CO_2H$ group attached in the 4-position are advantageously (but not necessarily) in the cis-configuration with respect to the piperidine ring.

In a particular embodiment, $R^a$ represents H.

Specific compounds in accordance with the invention are described in the Examples section appended hereto.

The compounds of formula I in which Z is $CO_2H$ are typically obtained by hydrolysis of the corresponding esters (1):

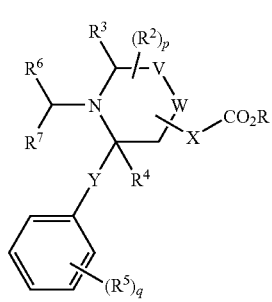

(1)

where R represents $C_{1-6}$alkyl such as methyl or ethyl and p, q, V, W, X, Y, $R^2$, $R^3$, $R^4$, $R^5$, $R^6$ and $R^7$ have the same meanings as before, e.g. by refluxing with LiOH in aqueous THF.

Corresponding compounds in which Z represents 1H-tetrazol-5-yl are obtainable by conversion of the esters (1) to the corresponding nitriles, followed by treatment with azidotrimethylsilane in refluxing toluene in the presence of tributyltin oxide. The conversion to the nitrile may be carried out by adding trimethylaluminium to a suspension of ammonium chloride in toluene, then adding the ester (1), refluxing the mixture, and treating with solid potassium sodium tartrate.

Compounds (1) may be obtained by reaction of compounds (2) with $R^6R^7CH$-L:

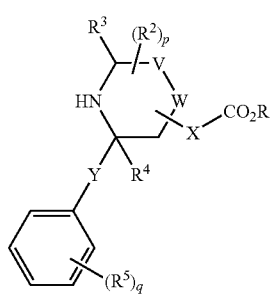

(2)

where L is a leaving group such as halide (especially bromide or iodide), tosylate, mesylate or triflate, and R, p, q, V, W, X, Y, $R^2$, $R^3$, $R^4$, $R^5$, $R^6$ and $R^7$ have the same meanings as before. Normal alkylating conditions may be employed, e.g. heating in DMF solution in the presence of base such as potassium carbonate.

Alternatively, compounds (2) may undergo reductive alkylation with precursors of the group $R^6R^7CH$— which contain an aldehyde or ketone functionality. In such cases, the compound (2) may be refluxed with $R^6$—CO—$R^7$ in toluene in the presence of an acid catalyst, with azeotropic removal of water, and the resulting adduct reduced using sodium triacetoxyborohydride. In a variant of this route, useful when $R^7$ is an alkyn-1-yl group, a compound (2) is reacted with $R^6$—CHO and $R^7$—H in the presence of gold(III) bromide, e.g. via microwave heating at 70° C. in water.

In another variant, the compound (2), $R^6$—CHO and benzotriazole are refluxed in toluene with azeotropic removal of water, and the resulting adduct reacted with $R^7$—Zn-Hal where Hal represents halide (preferably chloride) and $R^6$ and $R^7$ have the same meanings as before. The reaction is suitably carried out in an anhydrous aprotic solvent such as dichloromethane at reduced temperature, e.g. below 10° C.

Piperidines (2) in which V and W are both carbon atoms and $R^3$ and $R^4$ are H may be obtained by hydrogenation of the corresponding pyridines (3):

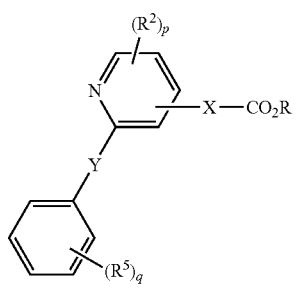

(3)

where R, p, q, X, Y, $R^2$ and $R^5$ have the same meanings as before, e.g. in methanolic HCl over a $PtO_2$ catalyst.

Pyridines (3) in which X is a bond and Y is a bond are obtainable by coupling of chloropyridines (4a) with arylboronic acids (5a):

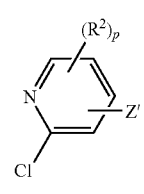

(4)

(a) Z' = $CO_2R$
(b) Z' = $CH_3$

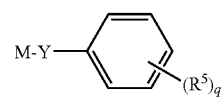

(5)

(a) M-Y = $B(OH)_2$
(b) M-Y = $BrZnCH_2$
(c) M-Y = HC≡C where R, p, q, $R^2$ and $R^5$ have the same meanings as before. The reaction takes place under standard Suzuki coupling conditions, e.g. in aqueous dimethoxyethane in the presence of sodium carbonate and $Pd(PPh_3)_4$.

Pyridines (3) in which X is a bond and Y is $CH_2$ are obtainable by coupling of chloropyridines (4a) with benzylzinc derivatives (5b). The reaction may be carried out at 0° C. to ambient temperature in THF in the presence of a nickel catalyst such as $(Ph_3P)_2NiCl_2$.

Pyridines (3) in which X is a bond and Y is $CH_2CH_2$ are obtainable by coupling of chloropyridines (4a) with alkynes (5c) followed by hydrogenation. The coupling may be carried out in the presence of CuI and a Pd(0) catalyst such as Pd $(Ph_3)_4$, e.g. in a mixture of dioxan and triethylamine with microwave heating. The hydrogenation takes place under similar conditions to the conversion of pyridines (3) to piperidines (2), and indeed is preferably combined with that process.

Pyridines (3) in which X is $CH_2$ may be obtained by elaboration of chloropyridines (4b) with (5a), (5b) or (5c) as described above, then treating the product with $CO(OR)_2$ in the presence of strong base such as lithium diisopropylamide, where R has the same meaning as before. Alternatively, the chloropyridines (4b) may be treated with $CO(OR)_2$ prior to the reaction with (5a), (5b) or (5c).

Piperidines of formula (2) in which V and W are both carbon atoms and $R^3$ and $R^4$ are H, X is a bond, p is 1 and $R^2$ is attached to the same ring position as the $CO_2R$ group are obtained by alkylation of the corresponding compounds in which p is 0 with $R^2$-L, where L has the same meaning as before. The reaction may be carried out in THF solution in the presence of strong base such as lithium hexamethyldisilazide (HMDS). During this procedure, it is preferable to protect the 1-position of the piperidine ring, e.g. as the BOC derivative.

An alternative route to esters (1) in which V and W are both carbon atoms and $R^3$ and $R^4$ are H, p is 0, X is $CH_2$ and the $CH_2CO_2R$ group is attached to the 4-position involves condensation of piperidones (6) with $(RO)_2P(O)CH_2CO_2R$, followed by hydrogenation of the resulting olefin (7):

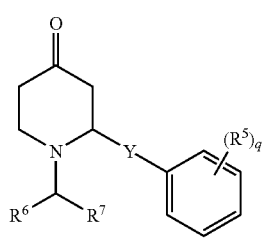

(6)

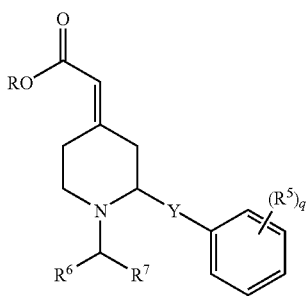

(7)

where R, Y, q, $R^5$, $R^6$ and $R^7$ have the same meanings as before. The condensation takes place in THF in the presence of NaH, while the hydrogenation may be carried out over a Pd/C catalyst in ethanol. Corresponding esters of formula (1) in which X is a bond may be obtained by treatment of ketones (6) with KHMDS and $Tf_2NPh$, then with CO and ROH in the presence of a Pd(II) catalyst, followed by hydrogenation of the resulting tetrahydropyridine derivative.

Ketones (6) are available by reduction of dihydropyridones (8):

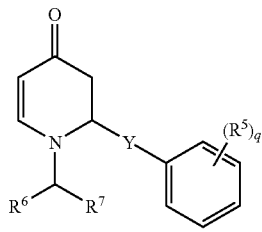

(8)

where Y, q, $R^5$, $R^6$ and $R^7$ have the same meanings as before. The reduction may be carried out using a borohydride reductant such as L-Selectride in THF at −78° C.

Compounds (8) are available by the Diels-Alder reaction between trans-1-methoxy-3-(trimethylsilyloxy)-1,3-butadiene and the imine formed from condensation of $R^6R^7CH—NH_2$ and an aldeyde (9):

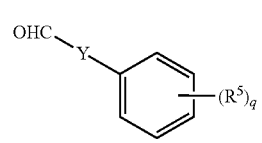

(9)

where Y, q, $R^5$, $R^6$ and $R^7$ have the same meanings as before. The cycloaddition may be carried out in acetonitrile at ambient temperature in the presence of In(III) triflate, followed by quenching with aqueous bicarbonate.

Alternatively, piperidones (6) may be obtained in a one-pot process by reacting the aforesaid imines with trimethyl[(1-methyleneprop-2-en-1-yl)oxy]silane (e.g. in dichloromethane at ambient temperature under an inert atmosphere), then adding tetrabutylammonium fluoride.

An alternative route to piperidines (2) in which V and W are both carbon atoms and $R^3$ and $R^4$ are H, p is 0, X is $CH_2$ and the $CH_2CO_2R$ group is attached to the 4-position involves elaboration of the dihydropyridones (10):

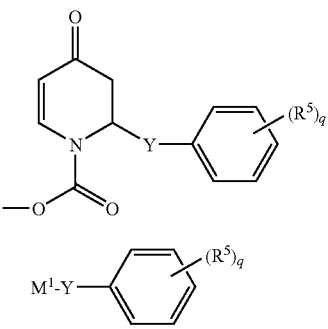

(10)

(11)

where Y, q and $R^5$ have the same meanings as before, in the manner described above for dihydropyridines (8), followed by removal of the benzyloxycarbonyl protecting group (e.g. by treatment with acid). Compounds (10) are available by a one-pot reaction of 4-methoxypyridine with benzyl chloroformate and organometallic derivatives (11), where $M^1$ is Li or Mg-halide, and Y, q and $R^5$ have the same meanings as before. The reaction takes place at reduced temperature (e.g. −25° C.) in a solvent such as THF.

In the above-described routes involving dihydropyridines (8) or (10), Y is preferably a bond.

The above-described routes involving dihydropyridines (8) or (10) may be adapted to provide products having an $R^2$ in the 3-position of the piperidine ring via alkylation of the compounds (8) or (10) with $R^2$-L, where $R^2$ and L have the same meanings as before. Said alkylation takes place under conventional conditions (e.g. in THF in the presence of lithium diisopropylamide).

Alternatively, the aforesaid routes may be adapted to provide products having an $R^2$ group in the 6-position of the piperidine ring via treatment of compounds (8) or (10) with $R^2$-Mg-halide in the presence of CuI, where $R^2$ has the same meaning as before. The reaction may be carried out in THF at reduced temperature (e.g. −78° C. to −10° C.).

In a further alternative, the aforesaid routes may be adapted to provide products in which the —$CH_2CO_2R$ group is attached at the 3-position of the piperidine ring via alkylation of compounds (8) or (10) with L-$CH_2CO_2R$, where L and R have the same meanings as before, followed by reduction of the keto group to $CH_2$. The alkylation takes place under conventional conditions, and reduction of the keto group is readily effected via treatment with 1,2-ethanedithiol to form the dithioketal, followed by treatment with Raney nickel.

An alternative route to piperidines of formula (1) in which V and W are both carbon atoms and $R^3$ and $R^4$ are both H, X is a bond, p is 0 and $CO_2R$ is attached to the 5-position involves cyclisation of dienes (12) followed by reduction of the resulting 1,2,3,6-tetrahydropyridine derivative:

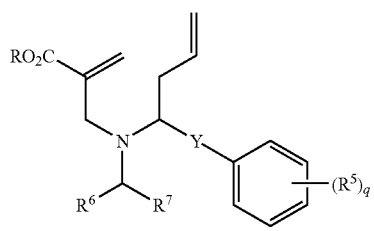

(12)

where R, Y, q, $R^5$, $R^6$ and $R^7$ have the same meanings as before. The cyclisation takes place in the presence of a Ru catalyst and the reduction may be effected by treatment with Mg in methanol. Dienes (12) are obtainable by alkylation of secondary amines (13) with the appropriate bromomethacrylate ester, and amines (13) are available by condensation of aldehydes (9) with $R^6R^7CH-NH_2$ and treatment of the product with allyltributylstannane:

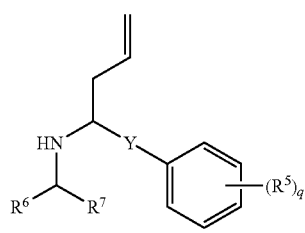

(13)

where Y, q, $R^5$, $R^6$ and $R^7$ have the same meanings as before.

Another route to piperidines of formula (1) in which V and W are both carbon atoms, p is 0, $R^3$ and $R^4$ are both H, X is a bond and $CO_2R$ is attached in the 4-position involves mono-decarboxylation of bis-esters (14):

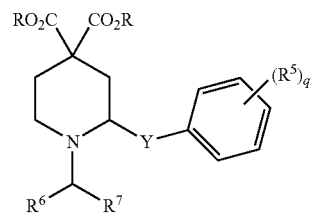

(14)

where R, Y, q, $R^5$, $R^6$ and $R^7$ have the same meanings as before. The reaction may be carried out by heating at about 160° C. with sodium chloride in DMSO. Subsequent reflux of the product with sodium methoxide in methanol causes epimerisation at the 4-position and enrichment with the cis-isomer at the expense of the trans-isomer. Bis-esters (14) are available from the reaction of amines $R^6R^7CH-NH_2$ with diketones (15):

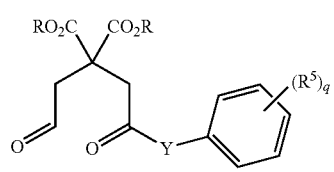

(15)

followed by reduction with sodium cyanoborohydride in a one-pot procedure, where R, Y, q, $R^5$, $R^6$ and $R^7$ have the same meanings as before. The first step may be carried out in dimethoxyethane in the presence of a tertiary amine and $TiCl_4$ at −78° C. with warming to ambient. The second step may be carried out by adding a methanolic solution of sodium cyanoborohydride to the reaction mixture at room temperature. Diketones (15) may be obtained by alkylation of the appropriate allylmalonate dialkyl ester with a compound of formula (16):

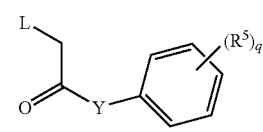

(16)

followed by ozonolysis of the allyl group, where L, R, Y, q and $R^5$ have the same meanings as before. The alkylation may be carried out in DMF in the presence of NaH (e.g. at ambient temperature). The ozonolysis may be effected by passing ozone-enriched oxygen through a dichloromethane solution of the substrate at −78° C., adding dimethyl sulfide, then stirring overnight at ambient temperature.

Piperidines of formula (2) in which $R^3$ and $R^4$ complete a —$CH_2CH_2$— bridge and Y is a bond may be obtained by elaboration of bicyclic ketones (17):

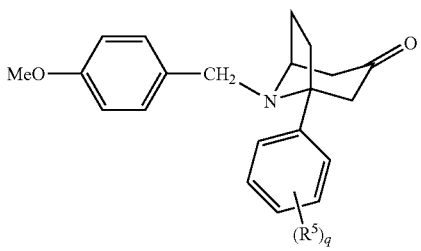

(17)

wherein q and $R^5$ have the same meanings as before, by the methods described above for the conversion of ketones (6) to esters (1), followed by removal of the protecting group 4-methoxybenzyl by hydrogenation.

The bicyclic ketones (17) are available by reaction of 4-methoxybenzylamine with acetonedicarboxylic acid, then treatment of the product in situ with a ketoaldehyde (18):

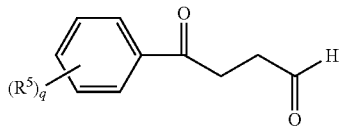

(18)

where $R^5$ and q have the same meanings as before.

A preferred route to piperazines of formula (1) in which V is a carbon atom and W is a nitrogen atom involves alkylation of compounds (19) with L-X'—$CO_2R$:

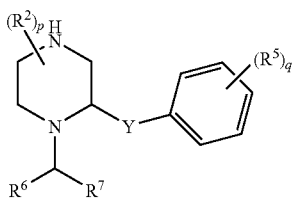

(19)

where X' is X that is other than a bond and all other variables are as defined previously. Compounds (19) are available from compounds (20):

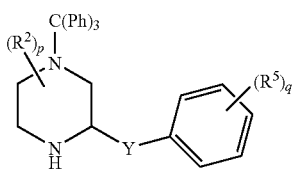

(20)

using the methods described previously for conversion of compounds (2) to compounds (1), followed by removal of the trityl group (e.g. by treatment with methanolic HCl). Compounds (20) are available via coupling of compounds (5a), (5b) or (5c) with the appropriate pyrazine derivatives in the manner described above for the synthesis of pyridines (3), followed by hydrogenation (as in the conversion of compounds (3) to compounds (2)) and tritylation by standard methods.

A preferred route to pyrrolidines of formula (1) in which V is a bond, p is 0 and X represents $CH_2$ involves the steps of (a) condensing an aldehyde (9) with t-butylsulphinamide and reacting the resulting imine with allylMgBr to provide the adduct (21a):

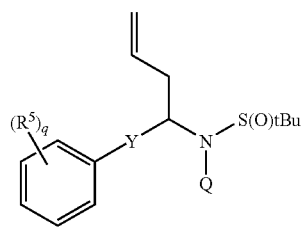

(21)

(a) Q = H
(b) Q = $CHR^6R^7$ (b) N-alkylation to provide compounds (21b) (e.g. by any of the methods described previously for converting (2) to (1));
(c) reaction with $CH_2$=CH—$CO_2R$ in the presence of a ruthenium catalyst (e.g. Zhan I), followed by treatment with methanolic HCl, to provide compounds (22a):

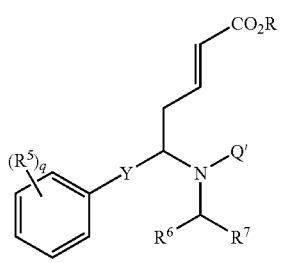

(22)

(a) Q' = H
(b) Q' = 1-benzotriazolylmethyl (d) reaction with 1-hydroxymethylbenzotriazole (e.g. in refluxing benzene with molecular sieves) to provide compounds (22b); and
(e) cyclisation by treatment with $SmI_2$ and t-butanol in THF at −78° C.

It will be readily apparent that several of the above-described routes are suitable for the synthesis of compounds of formula IV. Thus, in one preferred route to the ester precursors of compounds of formula IV, a piperidine of formula (2a), an aldehyde $R^6$—CHO and benzotriazole are refluxed in toluene with azeotropic removal of water, and the resulting adduct reacted with $R^7$—Zn-Hal

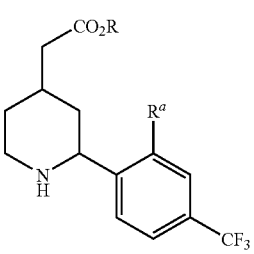

(2a)

where Hal represents halide (preferably chloride) and $R^a$, R, $R^6$ and $R^7$ have the same meanings as before. The reaction is suitably carried out in an anhydrous aprotic solvent such as dichloromethane at reduced temperature, e.g. below 10° C. Piperidines (2a) are available via coupling of pyridines (4b) with the appropriate boronic acid (5a) and further elaboration of the product as described previously.

In another preferred route to compounds of formula IV, a piperidine of formula (2a), an aldehyde $R^6$—CHO and a 1-alkyne are subjected to microwave heating in the presence of gold(III) bromide (e.g. at about 70° C.), providing compounds of formula IV in which $R^7$ is 1-alkynyl. If desired, the corresponding compounds in which $R^7$ is alkyl or alkenyl may be obtained by hydrogenation of the alkynyl derivatives (e.g. in ethyl acetate over a Pd/C catalyst).

In a third route to compounds of formula IV, the appropriate diketone of formula (15) (Y=a bond) is reacted with an amine of formula $R^6R^7CH$—$NH_2$ followed by treatment with sodium cyanoborohydride as described previously for the preparation of compounds (14). Thereafter, mono-decarboxylation (as described previously) and homologation (as described below) provide the compounds of formula IV.

Carboxylic acids of formula I in which X is a bond may be converted to the corresponding compounds in which X is $CH_2$ by standard methods of homologation, for example sequential treatment with oxalyl chloride; trimethylsilyldiazomethane and acetonitrile; ROH and silver benzoate; then hydrolysis of the resulting ester. Similar treatment of the corresponding compounds in which X is $CH_2$ provides the compounds in which X is $CH_2CH_2$. Esters of formula (1) in which X is $C(R^1)_2$ or $CH_2C(R^1)_2$ and at least one $R^1$ is other than H may be prepared by alkylation of the corresponding compounds in which each $R^1$ is H by standard methods.

Similarly, a given compound in accordance with formula I may be converted to a different compound in accordance with formula I by means of the standard techniques of bond formation or cleavage known to those skilled in the art of organic synthesis.

Where they are not themselves commercially available, the starting materials for the synthetic schemes described above are available by straightforward chemical modifications of commercially available materials.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary. Alternatively, racemic intermediates in the preparation of compounds of formula I may be resolved by the aforementioned techniques, and the desired enantiomer used in subsequent steps. For example, racemic piperidine derivatives (2a) may be resolved via salt formation with L-mandelic acid.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, $3^{rd}$ ed., 1999. The protecting groups may be removed at a convenient subsequent stage using methods known from the art.

The compounds of the invention have the useful property of modifying the action of γ-secretase on amyloid precursor protein so as to selectively reduce the formation of the 1-42 isoform of Aβ, and hence find use in the development of treatments for diseases mediated by Aβ(1-42), in particular diseases involving deposition of β-amyloid in the brain.

According to a further aspect of the invention there is provided the use of a compound according to formula I as defined above, or a pharmaceutically acceptable salt thereof, for the manufacture of a medicament for treatment or prevention of a disease associated with the deposition of β-amyloid in the brain.

The disease associated with deposition of Aβ in the brain is typically Alzheimer's disease (AD), cerebral amyloid angiopathy, HCHWA-D, multi-infarct dementia, dementia pugilistica or Down syndrome, preferably AD.

In a further aspect, the invention provides the use of a compound of Formula I as defined above, or a pharmaceutically acceptable salt thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42), A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n.* 18 (1993), 2386-2391). The MMSE is a brief quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry*, 141 (1984), 1356-64).

The compounds of Formula I are typically used in the form of pharmaceutical compositions comprising one or more compounds of Formula I and a pharmaceutically acceptable carrier. Accordingly, in a further aspect the invention provides a pharmaceutical composition comprising a compound of formula I as defined above, or a pharmaceutically acceptable salt thereof, and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ. Such additional compounds also include growth hormone secretagogues, as disclosed in WO 2004/110443.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671.), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of A β including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature*, 423 (2003), 435-9.

Alternatively, the amyloid modifier may be a compound which inhibits the aggregation of Aβ or otherwise attenuates is neurotoxicicity. Suitable examples include chelating agents such as clioquinol (Gouras and Beal, *Neuron*, 30 (2001), 641-2) and the compounds disclosed in WO 99/16741, in particular that known as DP-109 (Kalendarev et al, *J. Pharm. Biomed. Anal.*, 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 and the compound known as Alzhemed™ (Neurochem); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

EXAMPLES

The ability of the compounds of Formula I to selectively inhibit production of Aβ(1-42) was determined using the following assay:

Cell-Based γ-Secretase Assay

Human SH-SY5Y neuroblastoma cells overexpressing the direct γ-secretase substrate SPA4CT were induced with sodium butyrate (10 mM) for 4 hours prior to plating. Cells were plated at 35,000 cells/well/100 µl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 µl of these diluted compounds in $Me_2SO$ were further diluted into 182 µl dilution buffer (phenol red-free MEM/10% FBS, 50 mM HEPES, 1% Glutamine) and 10 µl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% $CO_2$, 10 µl and 50 µl media were transferred into a fresh Costar round-bottom 96-well plate for detection of Aβ(40) and Aβ(42) peptides, respectively. 40 µl Origen buffer (PBS, 2% BSA, 0.2% Tween-20) was added to the Aβ(40) wells followed by the addition of 25 µl the respective antibody premixes to the wells:

Aβ(40) premix: 1 µg/ml ruthenylated G2-10 antibody, 4 µg/ml biotinylated 4G8 antibody diluted in Origen buffer Aβ(42) premix: 0.5 μg/ml ruthenylated G2-11 antibody, 4 μg/ml biotinylated 4G8 antibody diluted in Origen buffer
(Biotinylated 4G8 Antibody Supplied by Signet Pathology Ltd; G2-10 and G2-11 Antibodies Supplied by Chemicon)

After overnight incubation of the assay plates on a shaker at 4° C., the Origen M8 Analyser (Igen Inc.) was calibrated according to the manufacturer's instructions. 25 μl of streptavidin magnetic bead (Dynal) premix (400 μg/ml streptavidin beads/ml in Origen buffer) was added to the assay plates and incubated on a shaker for 15 minutes. 150 μl Origen buffer was added to each well and the plates were read on the Origen M8 Analyser according to the manufacturer's instructions.

Cell viability was measured in the corresponding cells after removal of the media for the Aβ assays by a colorimetric cell proliferation assay (CellTiter 96™ AQ assay, Promega) utilizing the bioreduction of MTS (Owen's reagent) to formazan according to the manufacturer's instructions. Briefly, 5 μl of 10×MTS/PES was added to the remaining 50 μl of media before returning to the incubator. The optical density was read at 495 nm after ~4 hours.

$LD_{50}$ and $IC_{50}$ values for inhibition of Aβ(40) and Aβ(42) were calculated by nonlinear regression fit analysis using the appropriate software (eg. Excel fit). The total signal and the background were defined by the corresponding $Me_2SO$ and inhibitor controls.

The compounds listed in the following examples all gave $IC_{50}$ values for Aβ(1-42) inhibition that were at least 2-fold lower than the corresponding $IC_{50}$ values for Aβ(1-40) inhibition, typically at least 5-fold lower, and in the preferred cases at least 50-fold lower.

Intermediate 1: (±)-Methyl {2-[4-(trifluoromethyl)phenyl]piperidin-4-yl}acetate hydrochloride

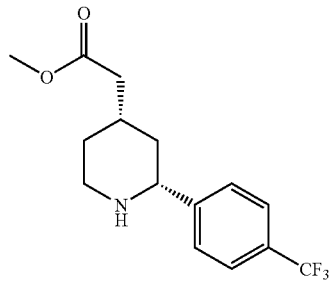 [SMILES: COC(=O)C[C@H]1CCN[C@@H](c2ccc(C(F)(F)F)cc2)C1]

Step 1:
4-Methyl-2-[4-(trifluoromethyl)phenyl]pyridine

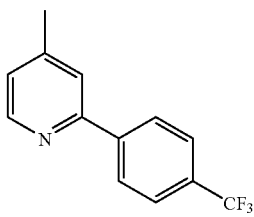 [SMILES: Cc1ccnc(-c2ccc(C(F)(F)F)cc2)c1]

A mixture of 2-chloro-4-methylpyridine (1.9 ml, 21.6 mmol) and 4-(trifluoromethyl)benzeneboronic acid (5.0 g, 26 mmol) in DME (40 ml) and aqueous $Na_2CO_3$ (2M, 40 ml) was degassed (Firestone® valve×3). Tetrakis(triphenylphosphine) palladium (0) (1.15 g, 1.0 mmol, 5 mol %) was added and following a further degassing (Firestone® valve×3) the mixture was heated at reflux for 16 hours. The reaction was cooled to room temperature diluted with $H_2O$ (100 ml) and EtOAc (150 ml). The mixture was filtered through a Celite® pad, washing through with EtOAc. The phases were separated and the aqueous layer was extracted with EtOAc (200 ml). The combined extracts were washed with $H_2O$ (100 ml) and brine (xl), then dried ($MgSO_4$), filtered and evaporated. The residue was purified by chromatography on silica, eluting with 10°/EtOAc/isohexane to give the ester (3.5 g, 68%) as a white solid. $^1$H NMR (360 MHz, $CDCl_3$) δ: 2.44 (3H, s), 7.13 (2H, d, J 5.0), 7.58 (1H, s), 7.72 (2H, d, J 8.2), 8.09 (2H, d, J 8.2), 8.57 (1H, d, J 5.0).

Step 2: Methyl {2-[4-(trifluoromethyl)phenyl]pyridin-4-yl}acetate

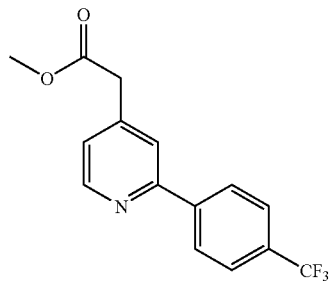 [SMILES: COC(=O)Cc1ccnc(-c2ccc(C(F)(F)F)cc2)c1]

A solution of LDA (2M in THF/heptane/ethyl benzene, 44 ml, 88 mmol) was added dropwise to a stirred solution of 4-methyl-2-[4-(trifluoromethyl)phenyl]pyridine (10.5 g, 44 mmol) in dry THF (300 ml) under $N_2$, such that the internal temperature remained <–70° C. After 1 hour at this temperature, dimethyl carbonate (8.9 ml, 106 mmol) was added. After 30 minutes the cooling bath was removed. When the internal temperature had reached –20° C. the reaction was transferred to a cold bath at –10° C., and then allowed to warm slowly to 0° C. After 1 hour at 0° C. the reaction was quenched with aqueous $NH_4Cl$ (half saturated, 100 ml). The reaction mixture was concentrated in vacuo. The residue was diluted with $H_2O$ (200 ml) and extracted with EtOAc (2×200 ml). The combined extracts were washed with brine (×1), then dried ($MgSO_4$), filtered and evaporated. The residue was purified by chromatography on silica, eluting with 10-30% EtOAc/isohexane to give the ester (9.2 g, 71%) as a pale yellow liquid. $^1$H NMR (400 MHz, $CDCl_3$) δ: 3.72 (2H, s), 3.75 (3H, s), 7.24 (1H, dd, J 1.4, 5.0), 7.72 (3H, t, J 8.4), 8.11 (2H, d, J 8.2), 8.68 (1H, d, J 5.0).

Step 3: (±)-Methyl {2-[4-(trifluoromethyl)phenyl]piperidin-4-yl}acetate hydrochloride A mixture of methyl {2-[4-(trifluoromethyl)phenyl]pyridin-4-yl}acetate (6.2 g, 21 mmol), $PtO_2$ (200 mg, 0.9 mmol) and HCl solution (4N in dioxane, 5.8 ml, 23 mmol) in MeOH (100 ml) was hydrogenated at 20 psi on a Parr® apparatus for 5 hours. The catalyst was removed by filtration and the filtrate evaporated in vacuo to give the desired piperidine as white solid (7.1 g, quant). $^1$H NMR (400 MHz, $CD_3OD$) δ: 1.58-1.72 (1H, m), 1.75-1.85 (1H, m), 2.08 (1H, d, J 14.2), 2.19 (1H, t, J 14.2), 2.28-2.38 (1H, m), 2.45 (2H, d, J 6.9), 3.24-3.32 (1H, m), 3.51-3.57 (1H, m), 3.67 (3H, s), 4.46 (1H, d, J 10.2), 7.72 (2H, d, J 8.3), 7.79 (2H, d, J 8.4).

The free base was obtained by treatment with $NaHCO_3$ (aq) and extraction in to DCM. The organic extracts were dried, filtered and evaporated.

Intermediates 1(a)-1(e)

The following were prepared by the same procedure as for Intermediate 1, using the appropriate arylboronic acid in Step 1:

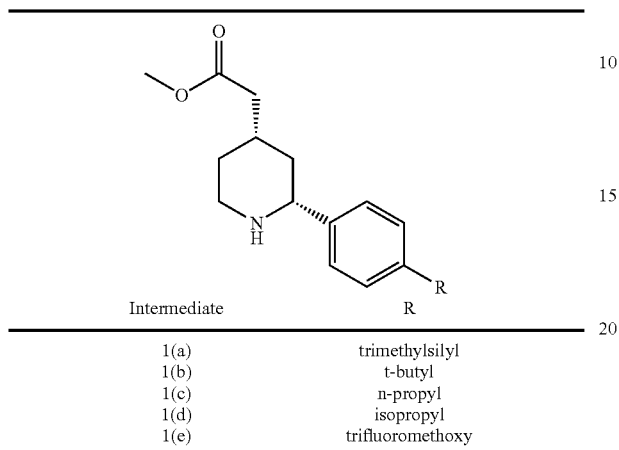

| Intermediate | R |
|---|---|
| 1(a) | trimethylsilyl |
| 1(b) | t-butyl |
| 1(c) | n-propyl |
| 1(d) | isopropyl |
| 1(e) | trifluoromethoxy |

Intermediate 2: (+)-M ethyl {(2S,4R)-2-[4-(trifluoromethyl)phenyl]piperidin-4-yl}acetate

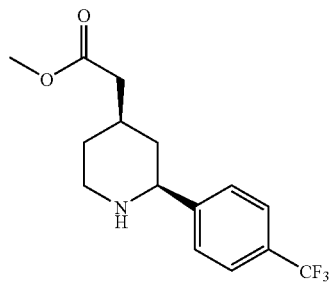 [SMILES: COC(=O)C[C@@H]1CCN[C@H](c2ccc(C(F)(F)F)cc2)C1]

(±)-cis Methyl 4-(trifluoromethyl)phenylpiperidin-4-yl) acetat (Intermediate 1 [free base], 32.6 g, 0.108 mol), was dissolved in hot isopropanol (100 ml) and the solution was added to a solution of L-(+)-mandelic acid (9 g, 0.054 mol) in hot isopropanol (170 ml) and the resulting solution was allowed to stand at room temperature overnight. A white crystalline solid was deposited (17.55 g, 36%) and was filtered. The mother liquors were evaporated and the residue was neutralized with sodium carbonate (2M, 100 ml) and extracted with dichloromethane (3×100 ml). The combined extracts were washed with brine, dried (MgSO$_4$), filtered and evaporated. This extract was dissolved in hot isopropanol (100 ml) and was added to a solution of D-(−)-mandelic acid (9 g, 0.054 mol) in hot isopropanol (170 ml); immediate crystallization occurred and the mixture was allowed to stand for 2 h. The white crystalline solid was isolated by filtration (21 g, 44%) and was recrystallised from isopropyl acetat (250 ml) to give the product (19.8 g, 40%) as a white crystalline material, ee>99.5%. This material was neutralized with sodium carbonate (2M, 100 ml and extracted with dichloromethane (3×100 ml). The combined extracts were washed with brine, dried (MgSO$_4$), filtered and evaporated to give the free base: $\alpha_D$ (c=1, MeOH)+23°; $^1$H NMR (360 MHz, CDCl$_3$) δ: 1.23 (6H, d, J 6.9), 2.88 (1H, qn, J 6.9), 4.27 (2H, s), 7.15-7.21 (4H, m), 7.71 (2H, d, J 8.2), 8.10 (2H, d, J 8.2).

Intermediate 3: (±)-Methyl {(2R*,3S*)-2-[4-(trifluoromethyl)phenyl]piperidin-3-yl}acetate

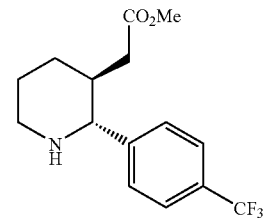 [SMILES: COC(=O)C[C@@H]1CCCN[C@H]1c1ccc(C(F)(F)F)cc1]

Step 1: (±)-Benzyl 4-oxo-2-[4-(trifluoromethyl)phenyl]-3,4-dihydropyridine-1(2H)-carboxylate

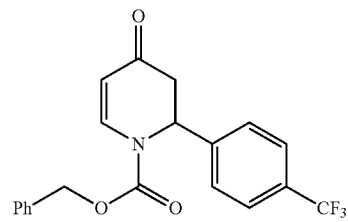

4-Trifluoromethyl bromobenzene (4.2 ml, 30 mmol) was added portionwise to magnesium turnings (0.729 g, 30 mmol) in dry THF (30 ml), and two drops of 1,2-dibromoethane were added to initiate the reaction. The resulting brown solution was cooled to −25° C. 4-Methoxypyridine (3.0 ml, 30 mmol) was added followed by benzyl chloroformate (4.3 ml, 30 mmol). The reaction was stirred for 30 mins at −20° C. then quenched with 2N HCl. After stirring for 10 mins the mixture was extracted with EtOAc (×3). The combined extracts were washed with brine, dried (MgSO$_4$), filtered and evaporated. The residue was purified by chromatography (silica, 10-40% EtOAc/hexanes) to give the dihydropyridine (9.30 g, 83%). $^1$H NMR (500 MHz, CDCl$_3$) δ: 2.77 (1H, d, J 16.6), 3.18 (1H, dd, J 7.7, 16.6), 5.20 (1H, d, J 12.0), 5.27 (1H, d, J 12.0), 5.42 (1H, d, J 8.3), 5.77 (1H, d, J 6.3), 7.24-7.37 (7H, m), 7.54 (2H, d, J 8.2), 8.00 (1H, m).

Step 2: (±)-Benzyl (2R*,3S*)-3-(2-methoxy-2-oxoethyl)-4-oxo-2-[4-(trifluoromethyl)phenyl]-3,4-dihydropyridine-1(2H)-carboxylate

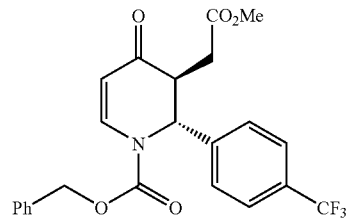 [SMILES: COC(=O)C[C@@H]1C(=O)C=CN(C(=O)OCc2ccccc2)[C@H]1c1ccc(C(F)(F)F)cc1]

A solution of the dihydropyridine from Step 1 (3.00 g, 8.0 mmol) in dry THF (80 ml) was cooled to −78° C. and lithium bis(trimethylsilyl)amide (1.0M in THF, 9.6 ml, 9.6 mmol) was added dropwise. After stirring at −78° C. for 1 hr, methyl bromoacetate (2.2 ml, 24 mmol) was added. The reaction was stirred at −78° C. for 1 hr then at 0° C. for 1.5 hrs. The reaction was quenched with saturated NH$_4$Cl solution. The mixture extracted with EtOAc (×3), the combined extracts were washed with brine, dried (MgSO$_4$), filtered and evaporated. The residue was purified by chromatography (silica, 40% Et$_2$O/hexanes) to give the ester (2.74 g, 77%). $^1$H NMR (360 MHz, CDCl$_3$) δ: 2.61-2.69 (2H, m), 3.15 (1H, dd, J 5.0, 9.8), 3.74 (3H, s), 5.18-5.28 (2H, m), 5.39 (1H, d, J 8.5), 5.70 (1H, s), 7.18-7.33 (7H, m), 7.54 (2H, d, J 8.3), 8.08 (1H, d, J 8.6).

Step 3: (±)-Benzyl (2R*,3S*)-3-(2-methoxy-2-oxo-ethyl)-4-oxo-2-[4-(trifluoromethyl)phenyl]piperidine-1-carboxylate

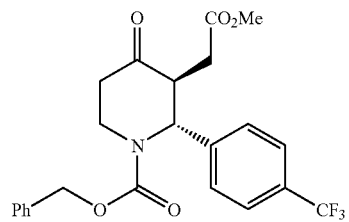 [SMILES: COC(=O)C[C@@H]1C(=O)CCN(C(=O)OCc2ccccc2)[C@H]1c1ccc(C(F)(F)F)cc1]

A solution of the enone from Step 2 (1.650 g, 3.7 mmol) in dry THF (40 ml) was cooled to −78° C. and L-selectride® (1.0M in THF, 4.6 ml, 4.6 mmol) was added. The reaction was stirred for 2 mins then quenched with saturated NH$_4$Cl solution. The mixture extracted with EtOAc (×3), the combined extracts were washed with brine, dried (MgSO$_4$), filtered and evaporated. The residue was purified by chromatography (silica, 40-50% Et$_2$O/hexanes) to give the ketone (1.473 g, 89%). $^1$H NMR (360 MHz, CDCl$_3$) δ: 2.24 (1H, dd, J 4.9, 16.8), 2.57-2.70 (3H, m), 3.46-3.52 (1H, m), 3.58 (3H, s), 3.80-3.89 (1H, m), 4.57 (1H, dd, J 5.2, 14.2), 4.93-4.98 (2H, m), 5.10 (1H, d, J 12.1), 7.07 (2H, s), 7.26-7.41 (5H, m), 7.57 (2H, d, J 8.1).

Step 4: (±)-Methyl {(6S*,7R*)-7-[4-(trifluoromethyl)phenyl]-1,4-dithia-8-azaspiro[4.5]dec-6-yl}acetate

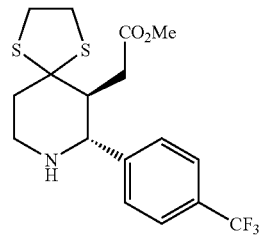 [SMILES: COC(=O)C[C@H]1[C@H](c2ccc(C(F)(F)F)cc2)NCCC12SCCS2]

A solution of the ketone from Step 3 (0.772 g, 1.7 mmol) in DCM (20 ml) was cooled to 0° C. and 1,2-ethanedithiol (0.43 ml, 5.1 mmol) and BF$_3$.OEt$_2$ (1.27 ml, 10 mmol) were added. The reaction was stirred at RT for 48 hrs then diluted with EtOAc. The mixture was washed with 1N NaOH solution then brine, dried (MgSO$_4$), filtered and evaporated. The residue was purified by chromatography (silica, 30% EtOAc/hexanes) to give the dithiane (0.420 g, 63%). $^1$H NMR (360 MHz, CDCl$_3$) δ: 2.03-2.11 (1H, m), 2.20-2.26 (1H, m), 2.35-2.43 (1H, m), 2.73-2.83 (2H, m), 3.06-3.16 (2H, m), 3.24 (3H, s), 3.25-3.32 (4H, m), 3.50 (1H, d, J 9.9), 7.47-7.58 (4H, m).

Step 5: (±)-Methyl {(2R*,3S*)-2-[4-(trifluoromethyl)phenyl]piperidin-3-yl}acetate Raney nickel (slurry in water) was added portionwise to a solution of the dithiane from Step 4 (0.418 g, 1.1 mmol) in MeOH (20 ml). The reaction was heated under reflux for 3 hrs then allowed to cool. The reaction was filtered through Hyflo® and the solvent was evaporated. The resulting mixture was extracted with DCM, dried (MgSO$_4$), filtered and evaporated. The residue was purified by chromatography (silica, 2% MeOH/DCM) to give the piperidine (0.168 g, 52%). $^1$H NMR (360 MHz, CDCl$_3$) δ: 1.21-1.26 (1H, m), 1.69-1.75 (2H, m), 1.90-2.10 (4H, m), 2.72-2.80 (1H, m), 3.16 (1H, m), 3.36 (1H, d, J 9.7), 3.50 (3H, s), 7.48 (2H, d, J 8.1), 7.57 (2H, d, J 8.2).

Example 1

{(2S,4R)-1-[(1S)-4-Methyl-1-(3-methylbutyl)pent-4-en-2-yn-1-yl]-2-[4-(trifluoromethyl)phenyl]piperidin-4-yl}acetic acid

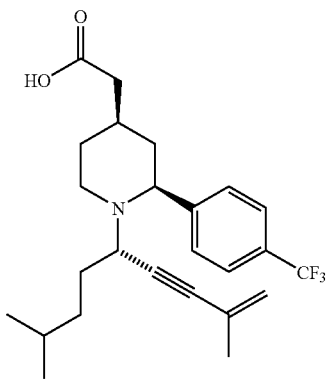 [SMILES: C=C(C)C#C[C@H](CCC(C)C)N1CC[C@@H](CC(=O)O)C[C@H]1c1ccc(C(F)(F)F)cc1]

Step 1: Methyl {(2S,4R)-1-[(1S)-4-methyl-1-(3-methylbutyl)pent-4-en-2-yn-1-yl]-2-[4-(trifluoromethyl)phenyl]piperidin-4-yl}acetate

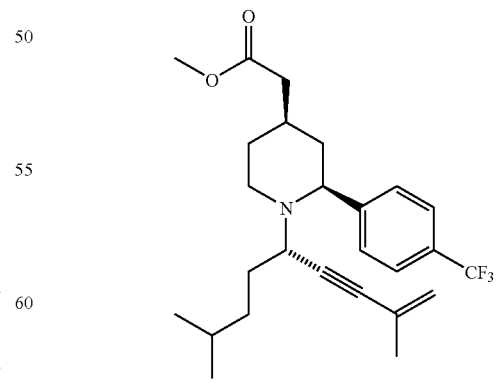

A mixture of (+)-methyl{(2S,4R)-2-[4-(trifluoromethyl)phenyl]piperidin-4-yl}acetate (Intermediate 2, 3.02 g, 10.0 mmol), 4-methylpentanal (2.1 g, 20.9 mmol) and gold (III)

bromide (440 mg, 1 mmol) were combined in water (10 ml) in a 20 ml microwave vial. After the mixture was deoxygenated by evacuate/fill N$_2$, 2-methylbut-1-en-3-yne (1.9 ml, 20.4 mmol) was added. The reaction was stirred and heated a 70° C. in the microwave for 30 min. The mixture was diluted with MeOH and loaded onto 5 SCX cartridges (10 g). Each cartridge was washed with MeOH (50 ml) then 2M NH$_3$ in MeOH (2×50 ml). The ammonia-methanol fractions were combined and evaporated. The residue was taken up in EtOAc and washed with brine (×1), then dried (Na$_2$SO$_4$), filtered and evaporated. The residue was combined with the product from a repeat experiment on the same scale and purified by chromatography (silica, 10% Et$_2$O/isohexane) to give the alkyne (9.1 g) a light yellow oil. $^1$H NMR (500 MHz, CDCl$_3$): δ 0.83 (6H, d, J 6.6), 1.07-1.22 (2H, m), 1.27-1.45 (3H, m), 1.51-1.58 (2H, m), 1.77-1.85 (2H, m), 1.91 (3H, s), 1.93-2.02 (1H, m), 2.19-2.29 (2H, m), 2.40-2.46 (1H, m), 2.94-2.98 (1H, m), 3.18 (1H, t, J 7.6), 3.50 (1H, dd, J 2.7, 11.2), 3.65 (3H, s), 5.19 (1H, m), 5.25 (1H, s), 7.45 (2H, d, J 7.4), 7.56 (2H, d, J 8.2); M/Z (ES$^+$) 420 (MH$^+$).

Step 2: {(2S,4R)-1-[(1S)-4-Methyl-1-(3-methylbutyl)pent-4-en-2-yn-1-yl]-2-[4-(trifluoromethyl)phenyl]piperidin-4-yl}acetic acid A solution of LiOH (67 mg, 2.8 mmol) in H$_2$O (1 ml) was added to a stirred solution of methyl {(2S,4R)-1-[(1S)-4-methyl-1-(3-methylbutyl)pent-4-en-2-yn-1-yl]-2-[4-(trifluoromethyl)phenyl]piperidin-4-yl}acetate (Step 1, 250 mg, 0.56 mmol) in THF (2 ml) at RT. The mixture was stirred at RT for 18 hrs, then at 60° C. for 3 hrs. After cooling to RT 2N HCl was added and the THF was removed in vacuo. The residue was partitioned between CH$_2$Cl$_2$/H$_2$O. The pH of the aqueous layer was adjusted to ~pH7 with saturated aqueous NaHCO$_3$. The aqueous layer was extracted with CH$_2$Cl$_2$ (×3). The combined extracts were dried (Na$_2$SO$_4$) filtered and evaporated. The residue was purified by chromatography (silica, 4% MeOH/CH$_2$Cl$_2$) to give the acid (228 mg) as a colourless foam. $^1$H NMR (500 MHz, CD$_3$OD): δ 0.83 (6H, d, J 6.6), 1.12-1.20 (2H, m), 1.33-1.43 (3H, m), 1.58 (2H, q, J 7.8), 1.80 (1H, dd, J 2.8, 12.8), 1.85-1.91 (5H, s), 2.18-2.26 (2H, m), 2.48 (1H, t, J 11.1), 2.98-3.04 (1H, m), 3.16 (1H, t, J 7.6), 3.55 (1H, dd, J 2.5, 11.3), 5.21 (1H, s), 5.24 (1H, s), 7.53 (2H, d, J 7.6), 7.62 (2H, d, J 8.2); M/Z (ES$^+$) 436 (MH$^+$).

Example 2

{(2S,4R)-1-[4-methyl-1-(3-methylbutyl)pentyl]-2-[4-(trifluoromethyl)phenyl]piperidin-4-yl}acetic acid

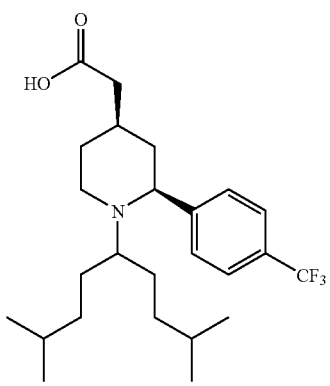 [SMILES: CC(C)CCC(CCC(C)C)N1CC[C@@H](CC(=O)O)C[C@H]1c1ccc(C(F)(F)F)cc1]

Step 1: Methyl {(2S,4R)-1-[4-methyl-1-(3-methylbutyl)pentyl]-2-[4-(trifluoromethyl)phenyl]piperidin-4-yl}acetate

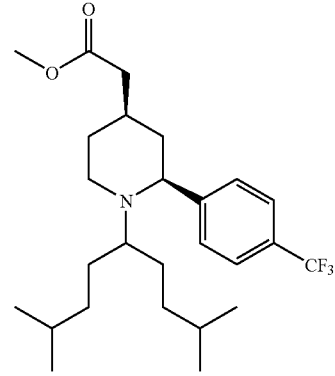 [SMILES: COC(=O)C[C@@H]1CCN(C(CCC(C)C)CCC(C)C)[C@H](c2ccc(C(F)(F)F)cc2)C1]

A solution of methyl {(2S,4R)-1-[(1S)-4-methyl-1-(3-methylbutyl)pent-4-en-2-yn-1-yl]-2-[4-(trifluoromethyl)phenyl]piperidin-4-yl}acetate (Example 1, Step 1, 8.4 g, 18.9 mmol) in MeOH (250 ml) was hydrogenated over Raney Nickel (~6 g) at 50 psi for 18 hrs. The catalyst was removed by filtration—washing with CH$_2$Cl$_2$. The filtrate was evaporated and the residue was partitioned between CH$_2$Cl$_2$/H$_2$O. The aqueous layer was extracted with CH$_2$Cl$_2$ (×1). The combined extracts were dried (Na$_2$SO$_4$), filtered and evaporated. The residue was purified by chromatography (silica, 3% EtOAc/isohexane) to give the alkane (6.24 g) as an oil. $^1$H NMR (500 MHz, CDCl$_3$): δ 0.64-0.74 (1H, m), 0.81 (6H, t J 6.5), 0.85 (6H, t, J 6.8), 0.93-0.97 (3H, m), 1.19-1.42 (7H, m), 1.52-1.58 (1H, m), 1.72-1.78 (2H, m), 1.86-1.94 (1H, m), 2.11-2.27 (4H, m), 2.92 (1H, brd, J 11.6), 3.58 (1H, dd, J2.6, 11.1), 3.64 (3H, s), 7.40 (2H, brs), 7.54 (2H, d, J 8.2). Further chromatography of mixed fractions (silica 2.5% EtOAc/isohexane) gave the cis alkene: methyl{(2S,4R)-1-[(1S,2Z)-4-methyl-1-(3-methylbutyl)pent-2-en-1-yl]-2-[4-(trifluoromethyl)phenyl]piperidin-4-yl}acetate (415 mg) as an oil. $^1$H NMR (500 MHz, CDCl$_3$): δ 0.68 (3H, d, J 6.6), 0.77 (3H, d, J 6.5) 0.83-0.86 (6H, m), 1.02-1.30 (4H, m), 1.37-1.43 (1H, m), 1.51-1.63 (3H, m), 1.71-1.78 (2H, m), 1.83-1.91 (1H, m), 2.13-2.27 (2H, m), 2.37-2.43 (1H, m), 3.02-3.06 (1H, m), 3.20 (1H, q, J 7.8), 3.42 (1H, dd, J 2.9, 11.1), 3.63 (3H, s), 5.20-5.28 (2H, m), 7.44 (2H, brd, J 7.5), 7.54 (2H, d, J 8.2).

Step 2: {(2S,4R)-1-[4-methyl-1-(3-methylbutyl)pentyl]-2-[4-(trifluoromethyl)phenyl]piperidin-4-yl}acetic acid A solution of LiOH (1.6 g, 67 mmol) in H$_2$O (15 ml) was added to a stirred solution of methyl {(2S,4R)-1-[4-methyl-1-(3-methylbutyl)pentyl]-2-[4-(trifluoromethyl)phenyl]piperidin-4-yl}acetate (Step 1, 6.0 g, 13.2 mmol) in THF (15 ml) at RT. The mixture was stirred and heated at 60° C. for 18 hrs. After cooling to R$_T$ 2N HCl (35 ml) was added and the THF was removed in vacuo. The residue was partitioned between CH$_2$Cl$_2$/H$_2$O. The pH of the aqueous layer was adjusted to pH7 with saturated aqueous NaHCO$_3$. The aqueous layer was extracted with CH$_2$Cl$_2$ (×3). The combined extracts were dried (Na$_2$SO$_4$) filtered and evaporated. The residue was purified by chromatography (silica, 4-8% MeOH/CH$_2$Cl$_2$) to give the acid (5.7 g) as a colourless solid. $^1$H NMR (500 MHz, CD$_3$OD): δ 0.68-0.75 (1H, m), 0.83-0.87 (12H, m), 0.97-1.09 (2H, m), 1.10-1.17 (1H, m), 1.32-1.50 (7H, m), 1.69-1.75 (1H, m), 1.86-2.00 (3H, m), 2.16-2.24 (2H, m), 2.25-2.31 (1H, m), 2.54 (1H, t, J 11.6), 3.17 (1H, d, J 11.8), 3.93 (1H, d, J 10.3), 7.54 (2H, brd, J 7), 7.65 (2H, d, J 8.2); M/Z (ES$^+$) 442 (MH$^+$).

Example 3

{(2S,4R)-1-[(1S,2Z)-4-methyl-1-(3-methylbutyl)pent-2-en-1-yl]-2-[4-(trifluoromethyl)phenyl]piperidin-4-yl}acetic acid

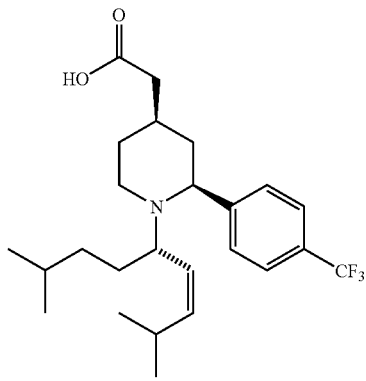 [SMILES: CC(C)/C=C\[C@H](CCC(C)C)N1CC[C@@H](CC(=O)O)C[C@H]1c1ccc(C(F)(F)F)cc1]

A solution of LiOH (60 mg, 2.5 mmol) in H$_2$O (1 ml) was added to a stirred solution of methyl {(2S,4R)-1-[(1S,2Z)-4-methyl-1-(3-methylbutyl)pent-2-en-1-yl]-2-[4-(trifluoromethyl)phenyl]piperidin-4-yl}acetate (Example 2, Step 1, 210 mg, 0.46 mmol) in THF (2 ml) at RT. The mixture was stirred at RT for 18 hrs, then at 60° C. for 3 hrs. After cooling to RT 2N HCl was added and the THF was removed in vacuo. The residue was partitioned between CH$_2$Cl$_2$ and H$_2$O. The pH of the aqueous layer was adjusted to ~pH7 with saturated aqueous NaHCO$_3$. The aqueous layer was extracted with CH$_2$Cl$_2$ (×3). The combined extracts were dried (Na$_2$SO$_4$) filtered and evaporated. The residue was purified by chromatography (silica, 4-10% MeOH/CH$_2$Cl$_2$) to give the acid (173 mg) as a colourless foam. $^1$H NMR (500 MHz, CD$_3$OD): δ 0.69 (3H, d, J 6.6), 0.81-0.87 (9H, m), 1.04-1.18 (2H, m), 1.25 (1H, q, J 12.1), 1.34-1.46 (3H, m), 1.56-1.68 (2H, m), 1.82-1.89 (3H, m), 2.13-2.21 (2H, m), 2.60 (1H, t, J 11.5), 3.23 (1H, brd, J 10), 3.38 (1H, q, J 8.7), 3.63 (1H, d, J 9.6), 5.28 (1H, t, J 10.6), 5.37 (1H, t, J 10.6), 7.53 (2H, d, J 7.7), 7.65 (2H, t, J 8.2); M/Z (ES$^+$) 440 (MH$^+$).

Example 4

{(2R,4S)-1-[(1R)-4-methyl-1-(4,4,4-trifluorobutyl)pent-4-en-2-yn-1-yl]-2-[4-(trifluoromethyl)phenyl]piperidin-4-yl}acetic acid

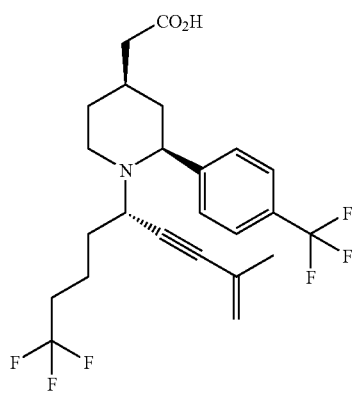 [SMILES: C=C(C)C#C[C@H](CCCC(F)(F)F)N1CC[C@@H](CC(=O)O)C[C@H]1c1ccc(C(F)(F)F)cc1]

Step 1

4,4,4-trifluorobutyl methanesulfonate

A solution of 4,4,4-trifluorobutanol (10.247 g, 80 mmol) and pyridine (12.9 ml, 160 mmol) in dry DCM (67 ml) was cooled to 0° C. and mesyl chloride (12.4 ml, 160 mmol) was added dropwise. The reaction was allowed to warm to rt and stirred for 2 hrs. The reaction was diluted with water and 2N HCl and extracted with DCM. The combined organics were washed sequentially with 2N HCl, sat. aq. NaHCO$_3$ and brine, dried (MgSO$_4$), filtered and evaporated. The residue was purified by chromatography (silica, 20-80% Et$_2$O/hexanes) to give the mesylate (15.5 g, 94%). 1H NMR (400 MHz, CDCl$_3$): δ 2.01-2.07 (2H, m), 2.21-2.33 (2H, m), 3.03 (3H, s), 4.29 (2H, t, J 6.1).

Step 2

5,5,5-trifluoropentanenitrile

A mixture of the mesylate from Step 1 (8.25 g, 40 mmol) and sodium cyanide (2.16 g, 44 mmol) in DMSO (80 ml) was heated at 60° C. for 2 hrs. The reaction was allowed to cool to rt and diluted with water and extracted with EtOAc. The combined extracts were washed with water (×2) then brine, dried (MgSO$_4$), filtered and evaporated. The residue was purified by chromatography (silica, 10-20% EtOAc/hexanes) to give the nitrile (2.049 g, 37%). 1H NMR (360 MHz, CDCl$_3$): δ 1.96 (2H, quintet, J 7.4), 2.22-2.36 (2H, m), 2.48 (2H, t, J 7.1).

Step 3

5,5,5-trifluoropentanal

A solution of the nitrile from Step 2 (2.040 g, 15 mmol) in dry DCM (60 ml) was cooled to −78° C. and a solution of diisobutylaluminium hydride (1.5M in PhMe, 10 ml, 15 mmol) was added at a rate such that the temperature was kept below −70° C. The reaction was stirred at −78° C. for 1.5 hrs then quenched with MeOH (2 ml). The reaction was allowed to warm to rt and sat. potassium sodium tartrate solution was added. The mixture was stirred for 30 mins then extracted with Et$_2$O. The combined extracts were washed with brine, dried (MgSO$_4$), filtered and evaporated. The residue was purified by chromatography (silica, 10% Et$_2$O/hexanes) to give a 1.3:1 mixture of the aldehyde:nitrile (0.439 g). 1H NMR (500 MHz, CDCl$_3$): δ 1.89 (2H, quintet, J 7.5), 2.12-2.18 (2H, m), 2.59 (2H, t, J 7.1), 9.79 (1H, s).

Step 4

Methyl {(2R,4S)-1-[(1R)-4-methyl-1-(4,4,4-trifluorobutyl)pent-4-en-2-yn-1-yl]-2-[4-(trifluoromethyl)phenyl]piperidin-4-yl}acetate

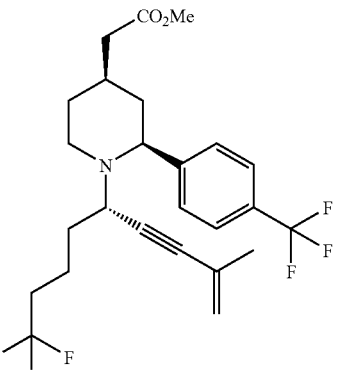

A mixture of Intermediate 2 (0.301 g, 1.0 mmol), 2-methyl-1-buten-3-yne (0.19 ml, 2.0 mmol), the aldehyde/nitrile mixture from Step 3 (0.360 g, approx. 1.5 mmol) and AuBr$_3$ (44 mg, 0.1 mmol) in water (11.0 ml) was heated at 70° C. in the microwave for 20 mins. The reaction mixture was loaded onto an SCX cartridge and washed with MeOH. The MeOH washings were discarded and the crude product was eluted with 2N NH$_3$ in MeOH. The eluent was concentrated, diluted with EtOAc, washed with brine, dried (MgSO$_4$), filtered and evaporated. The residue was purified by chromatography (silica, 5-10% EtOAc/hexanes) to give the enyne (0.372 g, 76%). M/Z 490 (MH$^+$).

Step 5

{(2R,4S)-1-[(1R)-4-methyl-1-(4,4,4-trifluorobutyl) pent-4-en-2-yn-1-yl]-2-[4-(trifluoromethyl)phenyl] piperidin-4-yl}acetic acid A solution of the ester from Step 4 (40 mg, 0.08 mmol) in aq. NaOH (4N, 1 ml) and MeOH (2 ml) was stirred at rt for 16 hrs. The reaction mixture was acidified to pH6 with 2N HCl, concentrated in vacuo then extracted with DCM. The combined extracts were washed with brine, dried (MgSO$_4$), filtered and evaporated. The residue was purified by chromatography (silica, 2-5% MeOH/DCM) to give the acid (37 mg, 95%). 1H NMR (360 MHz, CD$_3$OD): δ 1.34-1.47 (1H, m), 1.51-1.65 (1H, m), 1.7-1.91 (4H, m), 1.91 (3H, s), 1.91-2.06 (2H, m), 2.18-2.29 (2H, m), 2.49 (1H, t, J 12.0), 3.00 (1H, d, J 11.3), 3.23 (1H, t, J 7.1), 3.56 (1H, d, J 10.7), 5.24 (2H, d, J 11.1), 7.53 (2H, d, J 7.9), 7.62 (2H, d, J 8.0).

Example 5

{(2R,4S)-1-[(1R)-5,5,5-trifluoro-1-(3-methylbutyl) pentyl]-2-[4-(trifluoromethyl)phenyl]piperidin-4-yl}acetic acid

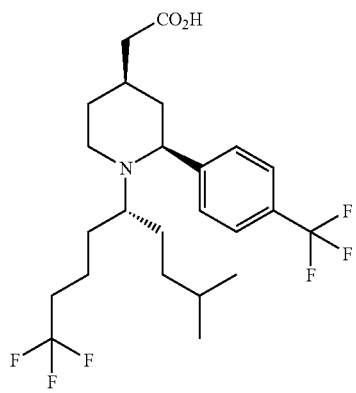 [SMILES: CC(C)CC[C@H](CCCC(F)(F)F)N1CC[C@@H](CC(=O)O)C[C@H]1c1ccc(C(F)(F)F)cc1]

Step 1 methyl {(2R,4S)-1-[(1R)-5,5,5-trifluoro-1-(3-methylbutyl)pentyl]-2-[4-(trifluoromethyl)phenyl]piperidin-4-yl}acetate

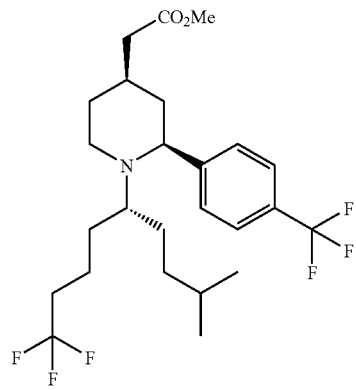 [SMILES: COC(=O)C[C@@H]1CCN([C@@H](CCCC(F)(F)F)CCC(C)C)[C@H](c2ccc(C(F)(F)F)cc2)C1]

The enyne from Example 4 Step 4 (0.332 g, 0.7 mmol) was taken up in MeOH (20 ml) and hydrogenated in a Parr™ apparatus in the presence of Raney-nickel under 50 psi of H$_2$-pressure for 6 hrs. The catalyst was removed by filtration and the filtrate was evaporated to give the ester (0.315 g, 94%). M/Z 497 (MH$^+$).

Step 2

{(2R,4S)-1-[(1R)-5,5,5-trifluoro-1-(3-methylbutyl) pentyl]-2-[4-(trifluoromethyl)phenyl]piperidin-4-yl}acetic acid The ester from Step 1 (0.315 g, 0.6 mmol) was hydrolysed using the procedure in Example 4 Step 5 to give the acid (0.247 g, 81%). 1H NMR (400 MHz, CD$_3$OD): δ 0.65-0.71 (1H, m), 0.83 (3H, d, J 6.5), 0.84 (3H, d, J 6.6), 0.95-1.11 (2H, m), 1.29-1.53 (6H, m), 1.67-2.07 (7H, m), 2.17-2.27 (3H, m), 2.39 (1H, t, J 11.2), 3.04 (1H, d, J 11.7), 3.75 (1H, d, J 8.9), 7.51 (2H, d, J 7.7), 7.62 (2H, d, J 8.2).

Examples 6-22

The following compounds were made by the procedures in Example 4 Steps 4 and 5, using Intermediate 1 and the appropriate aldehydes (2 eq.) and alkynes (2 eq.).

| Example | Structure | Name | M/Z ES$^+$ [MH]$^+$ |
|---|---|---|---|
| 6 | 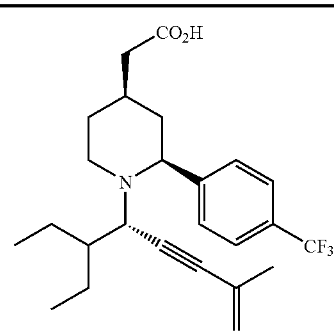 | {(2S*,4R*)-1-[(1R* or 1S*)-1-(1-ethylpropyl)-4-methylpent-4-en-2-yn-1-yl]-2-[4-(trifluoromethyl)phenyl]piperidin-4-yl}acetic acid | 436 |

| Example | Structure | Name | M/Z ES⁺ [MH]⁺ |
|---|---|---|---|
| 7 | 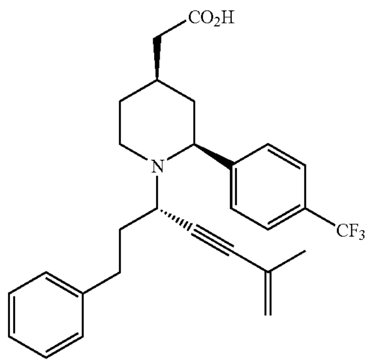 [SMILES: C=C(C)C#C[C@H](CCc1ccccc1)N1CC[C@@H](CC(=O)O)C[C@H]1c1ccc(C(F)(F)F)cc1] | {(2S*,4R*)-1-[(1R* or 1S*)-4-methyl-1-(2-phenylethyl)pent-4-en-2-yn-1-yl]-2-[4-(trifluoromethyl)phenyl]piperidin-4-yl}acetic acid | 470 |
| 8 | 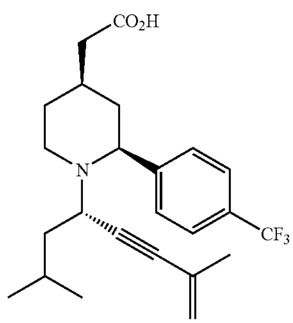 [SMILES: C=C(C)C#C[C@H](CC(C)C)N1CC[C@@H](CC(=O)O)C[C@H]1c1ccc(C(F)(F)F)cc1] | {(2S*,4R*)-1-[(1R* or 1S*)-1-isobutyl-4-methylpent-4-en-2-yn-1-yl]-2-[4-(trifluoromethyl)phenyl]piperidin-4-yl}acetic acid | 422 |
| 9 | 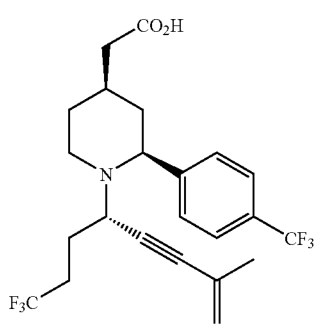 [SMILES: C=C(C)C#C[C@H](CCC(F)(F)F)N1CC[C@@H](CC(=O)O)C[C@H]1c1ccc(C(F)(F)F)cc1] | {(2S*,4R*)-1-[(1R* or 1S*)-4-methyl-1-(3,3,3-trifluoropropyl)pent-4-en-2-yn-1-yl]-2-[4-(trifluoromethyl)phenyl]piperidin-4-yl}acetic acid | 462 |
| 10 | 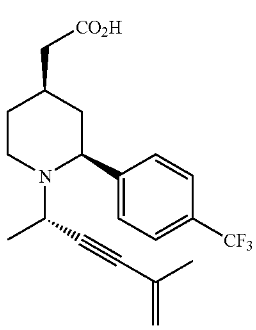 [SMILES: C=C(C)C#C[C@H](C)N1CC[C@@H](CC(=O)O)C[C@H]1c1ccc(C(F)(F)F)cc1] | {(2S*,4R*)-1-[(1R* or 1S*)-1,4-dimethylpent-4-en-2-yn-1-yl]-2-[4-(trifluoromethyl)phenyl]piperidin-4-yl}acetic acid | 380 |

-continued

| Example | Structure | Name | M/Z ES+ [MH]+ |
|---|---|---|---|
| 11 | 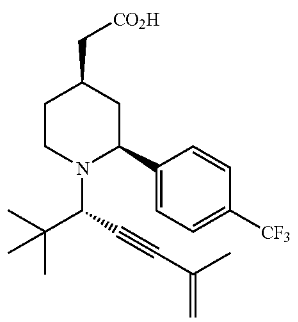 [SMILES: C=C(C)C#C[C@@H](N1CC[C@@H](CC(=O)O)C[C@H]1c1ccc(C(F)(F)F)cc1)C(C)(C)C] | {(2S*,4R*)-1-[(1R* or 1S*)-1-tert-butyl-4-methylpent-4-en-2-yn-1-yl]-2-[4-(trifluoromethyl)phenyl]piperidin-4-yl}acetic acid | 422 |
| 12 | 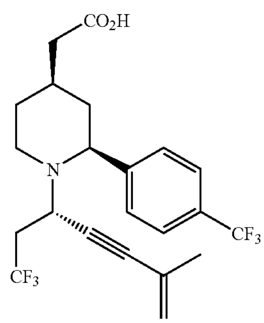 [SMILES: C=C(C)C#C[C@H](CC(F)(F)F)N1CC[C@@H](CC(=O)O)C[C@H]1c1ccc(C(F)(F)F)cc1] | {(2S*,4R*)-1-[(1R* or 1S*)-4-methyl-1-(2,2,2-trifluoroethyl)pent-4-en-2-yn-1-yl]-2-[4-(trifluoromethyl)phenyl]piperidin-4-yl}acetic acid | 448 |
| 13 | 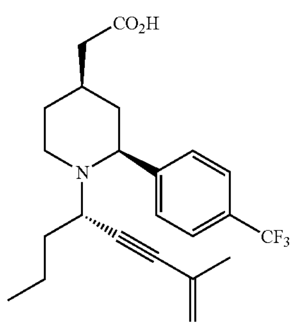 [SMILES: C=C(C)C#C[C@H](CCC)N1CC[C@@H](CC(=O)O)C[C@H]1c1ccc(C(F)(F)F)cc1] | {(2S*,4R*)-1-[(1R* or 1S*)-4-methyl-1-propylpent-4-en-2-yn-1-yl]-2-[4-(trifluoromethyl)phenyl]piperidin-4-yl}acetic acid | 408 |
| 14 | 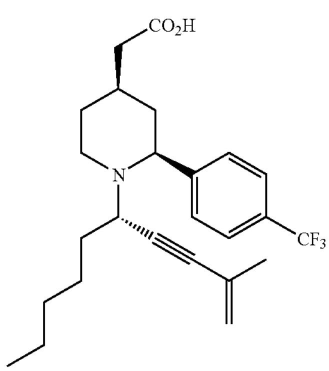 [SMILES: C=C(C)C#C[C@H](CCCCC)N1CC[C@@H](CC(=O)O)C[C@H]1c1ccc(C(F)(F)F)cc1] | {(2S*,4R*)-1-[(1R* or 1S*)-1-(3-methylbut-3-en-1-yn-1-yl)hexyl]-2-[4-(trifluoromethyl)phenyl]piperidin-4-yl}acetic acid | 436 |

-continued

| Example | Structure | Name | M/Z ES+ [MH]+ |
|---|---|---|---|
| 15 | 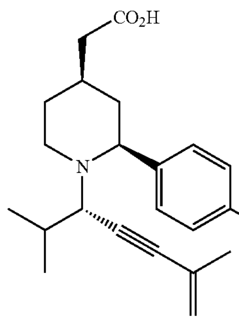 | {(2S*,4R*)-1-[(1R* or 1S*)-1-isopropyl-4-methylpent-4-en-2-yn-1-yl]-2-[4-(trifluoromethyl)phenyl]piperidin-4-yl}acetic acid | 408 |
| 16 | 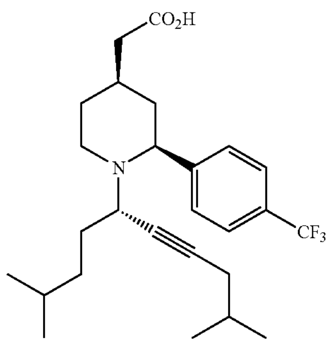 [SMILES: CC(C)CC#C[C@H](CCC(C)C)N1CC[C@@H](CC(=O)O)C[C@H]1c1ccc(C(F)(F)F)cc1] | {(2S*,4R*)-1-[(1R* or 1S*)-5-methyl-1-(3-methylbutyl)hex-2-yn-1-yl]-2-[4-(trifluoromethyl)phenyl]piperidin-4-yl}acetic acid | 452 |
| 17 | 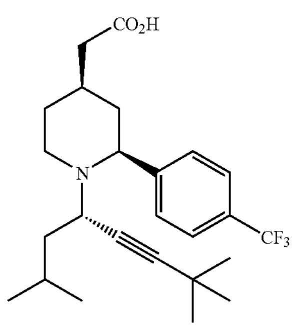 [SMILES: CC(C)C[C@@H](C#CC(C)(C)C)N1CC[C@@H](CC(=O)O)C[C@H]1c1ccc(C(F)(F)F)cc1] | {(2S*,4R*)-1-[(1R* or 1S*)-1-isobutyl-4,4-dimethylpent-2-yn-1-yl]-2-[4-(trifluoromethyl)phenyl]piperidin-4-yl}acetic acid | 438 |
| 18 | 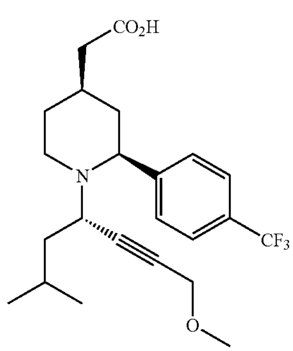 [SMILES: COCC#C[C@H](CC(C)C)N1CC[C@@H](CC(=O)O)C[C@H]1c1ccc(C(F)(F)F)cc1] | {(2S*,4R*)-1-[(1R* or 1S*)-1-isobutyl-4-methoxybut-2-yn-1-yl]-2-[4-(trifluoromethyl)phenyl]piperidin-4-yl}acetic acid | 426 |

-continued

| Example | Structure | Name | M/Z ES+ [MH]+ |
|---------|-----------|------|---------------|
| 19 | 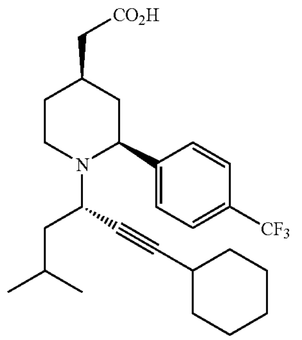 [SMILES: CC(C)C[C@@H](C#CC1CCCCC1)N1CC[C@@H](CC(=O)O)C[C@H]1c1ccc(C(F)(F)F)cc1] | {(2S*,4R*)-1-[(1R* or 1S*)-1-(cyclohexylethynyl)-3-methylbutyl]-2-[4-(trifluoromethyl)phenyl]piperidin-4-yl}acetic acid | 464 |
| 20 | 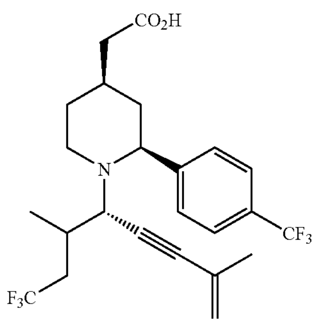 [SMILES: C=C(C)C#C[C@H](C(C)CC(F)(F)F)N1CC[C@@H](CC(=O)O)C[C@H]1c1ccc(C(F)(F)F)cc1] | {(2S*,4R*)-1-[(1R* or 1S*)-4-methyl-1-(3,3,3-trifluoro-1-methylpropyl)pent-4-en-2-yn-1-yl]-2-[4-(trifluoromethyl)phenyl]piperidin-4-yl}acetic acid | 476 |
| 21 | 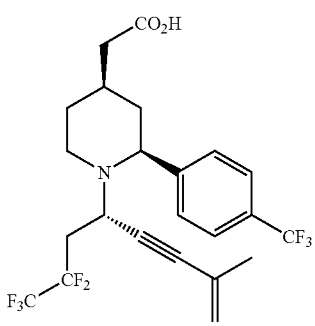 [SMILES: C=C(C)C#C[C@H](CC(F)(F)C(F)(F)F)N1CC[C@@H](CC(=O)O)C[C@H]1c1ccc(C(F)(F)F)cc1] | {(2S*,4R*)-1-[(1R* or 1S*)-4-methyl-1-(2,2,3,3,3-pentafluoropropyl)pent-4-en-2-yn-1-yl]-2-[4-(trifluoromethyl)phenyl]piperidin-4-yl}acetic acid | 498 |
| 22 | 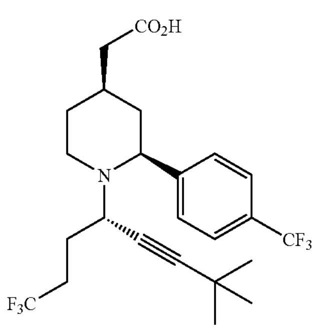 [SMILES: CC(C)(C)C#C[C@H](CCC(F)(F)F)N1CC[C@@H](CC(=O)O)C[C@H]1c1ccc(C(F)(F)F)cc1] | {(2S*,4R*)-1-[(1R* or 1S*)-4,4-dimethyl-1-(3,3,3-trifluoropropyl)pent-2-yn-1-yl]-2-[4-(trifluoromethyl)phenyl]piperidin-4-yl}acetic acid | 478 |

Examples 23-27

The following compounds were made by the procedures in Example 4 Step 4 and Example 5 Steps 1 and 2, using either Intermediate 2 or Intermediate 3 and the appropriate aldehyde.

| Example | Structure | Name | M/Z ES+ [MH]+ |
|---|---|---|---|
| 23 | 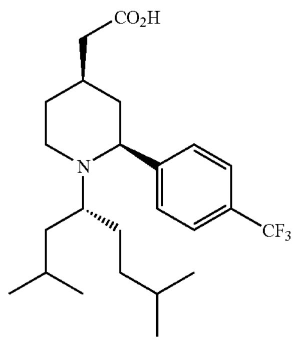 [SMILES: CC(C)CC[C@H](CC(C)C)N1CC[C@@H](CC(=O)O)C[C@H]1c1ccc(C(F)(F)F)cc1] | {(2S,4R)-1-[(1R)-1-isobutyl-4-methylpentyl]-2-[4-(trifluoromethyl)phenyl]piperidin-4-yl}acetic acid | 428 |
| 24 | 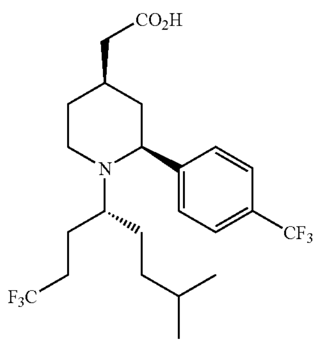 [SMILES: CC(C)CC[C@H](CCC(F)(F)F)N1CC[C@@H](CC(=O)O)C[C@H]1c1ccc(C(F)(F)F)cc1] | {(2S,4R)-1-[(1R)-4-methyl-1-(3,3,3-trifluoropropyl)pentyl]-2-[4-(trifluoromethyl)phenyl]piperidin-4-yl}acetic acid | 468 |
| 25 | 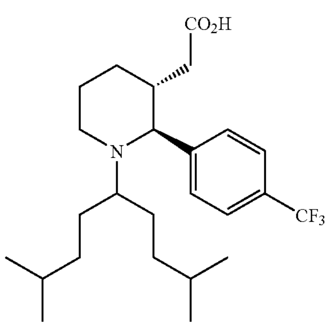 [SMILES: CC(C)CCC(CCC(C)C)N1CCC[C@H](CC(=O)O)[C@H]1c1ccc(C(F)(F)F)cc1] | {(2S*,3R*)-1-[4-methyl-1-(3-methylbutyl)pentyl]-2-[4-(trifluoromethyl)phenyl]piperidin-3-yl}acetic acid | 442 |
| 26 | 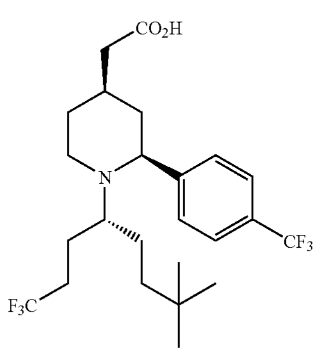 [SMILES: CC(C)(C)CC[C@H](CCC(F)(F)F)N1CC[C@@H](CC(=O)O)C[C@H]1c1ccc(C(F)(F)F)cc1] | {(2S,4R)-1-[(1R)-4,4-dimethyl-1-(3,3,3-trifluoropropyl)pentyl]-2-[4-(trifluoromethyl)phenyl]piperidin-4-yl}acetic acid | 482 |

| Example | Structure | Name | M/Z ES+ [MH]+ |
|---|---|---|---|
| 27 | 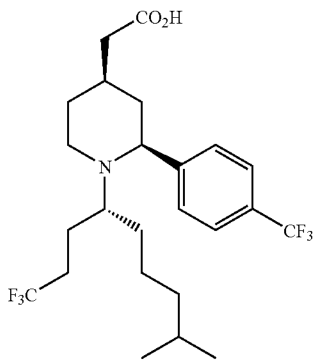 [SMILES: CC(C)CCC[C@H](CCC(F)(F)F)N1CC[C@@H](CC(=O)O)C[C@H]1c1ccc(C(F)(F)F)cc1] | {(2S,4R)-1-[(1R)-5-methyl-1-(3,3,3-trifluoropropyl)hexyl]-2-[4-(trifluoromethyl)phenyl]piperidin-4-yl}acetic acid | 482 |

Example 28

{(2S,4R)-1-{(1R)-1-[(Benzyloxy)methyl]-4-methyl-pent-4-en-2-yn-1-yl}-2-[4-(trifluoromethyl)phenyl]piperidin-4-yl}acetic acid A mixture of Intermediate 2 (1.1 g, 3.65 mmol), benzyloxyacetaldehyde (1.097 g, 7.30 mmol), gold(III) bromide (0.159 g, 0.365 mmol) and 2-methyl-1-buten-3-yne (0.681 ml, 7.30 mmol) were combined in water (3 ml) in a 20 ml microwave vial. The vial was sealed and the reaction was heated at 70° C. for 30 minutes in the microwave. The mixture was diluted with MeOH and loaded on to a SCX cartridge (10 g). This was washed with MeOH (~50 ml), then the products were eluted with 2M $NH_3$ in MeOH. The ammonia/methanol fraction was evaporated. The residue was partitioned between EtOAc/brine. The aqueous layer was extracted with EtOAc (×3). The combined extracts were washed with brine (×1), dried ($Na_2SO_4$), filtered and evaporated. The residue was purified by chromatography (silica, 5-8-10% EtOAc/isohexane) to give the ester (1.4 g) as a colourless oil. This material was hydrolysed with LiOH in THF/water in the usual way to give the title compound. M/Z 486 (MH+).

Example 29

{(2S,4R)-1-[(1R)-1-(Isopropoxymethyl)-4-methyl-pentyl]-2-[4-(trifluoromethyl)phenyl]piperidin-4-yl}acetic acid

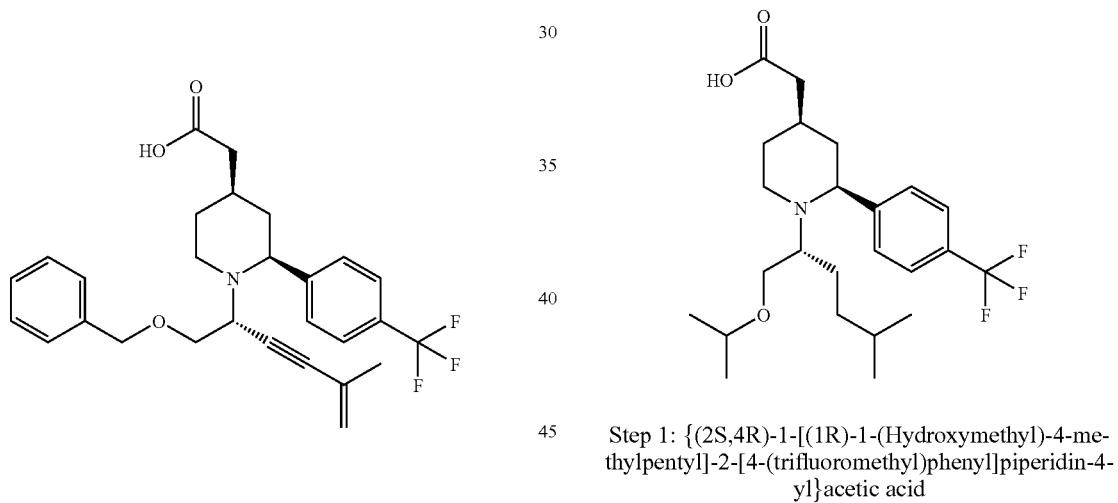

Step 1: {(2S,4R)-1-[(1R)-1-(Hydroxymethyl)-4-methylpentyl]-2-[4-(trifluoromethyl)phenyl]piperidin-4-yl}acetic acid A solution of methyl {(2S,4R)-1-{(1R)-1-[(benzyloxy)methyl]-4-methylpent-4-en-2-yn-1-yl}-2-[4-(trifluoromethyl)phenyl]piperidin-4-yl}acetate (Example 28, 1.4 g, 2.80 mmol) in MeOH (15 ml) was hydrogenated over Raney nickel (~1 g) at 50 psi on the Parr overnight at room temperature. MS showed mostly desired product, but still some alkene. Extra Raney nickel (~1 g) was added and the hydrogenation was continued for a further 5 hours. MS showed the reduction to be almost complete. The catalyst was removed by filtration, washing with MeOH. The filtrate was evaporated. The residue was partitioned between DCM and water. The aqueous layer was extracted with DCM (×3). The combined extracts were dried ($Na_2SO_4$), filtered and evaporated to give the alkane (1.16 g) as an oil. This material was used without further purification. A solution of benzyl ether (above, 1.16 g, 2.294 mmol) in acetic acid (25 ml) was hydrogenated at 50 psi over 10% palladium on carbon (150 mg, 0.141 mmol) on the Parr at room temperature overnight. The catalyst was removed by filtration—washing with MeOH. The filtrate was evaporated—azeotroping with PhMe (×2). The residue was partitioned between DCM and saturated aqueous $NaHCO_3$. The aqueous layer was extracted with DCM (×3). The combined extracts were dried ($Na_2SO_4$), filtered and evaporated. The residue was purified by chromatography (silica, 10-20-40% EtOAc/isohexanes) to give the alcohol. (795 mg) as an oil. This material was hydrolysed with NaOH in MeOH to give {(2S,4R)-1-[(1R)-1-(hydroxymethyl)-4-methylpentyl]-2-[4-(trifluoromethyl)phenyl]piperidin-4-yl}acetic acid, M/Z 402 ($MH^+$).

Step 2: {(2S,4R)-1-[(1R)-1-(Isopropoxymethyl)-4-methylpentyl]-2-[4-(trifluoromethyl)phenyl]piperidin-4-yl}acetic acid Powdered KOH (375 mg, 6.68 mmol) was taken up in dry DMSO (1 ml) at RT under $N_2$. The mixture was stirred for 10 minutes before the addition of {(2S,4R)-1-[(1R)-1-(hydroxymethyl)-4-methylpentyl]-2-[4-(trifluoromethyl)phenyl]piperidin-4-yl acetic}acid (Step 1, 67 mg, 0.167 mmol) in dry DMSO (0.5+0.5+0.5 ml), followed by 2-iodopropane (0.334 ml, 3.34 mmol). After 24 hr MS further 2-iodopropane (0.334 ml, 3.34 mmol) was added and the reaction was maintained at RT for 3 days. The reaction was quenched with saturated aqueous $NH_4Cl$ and then partitioned between DCM and $H_2O$. The aqueous layer was extracted with DCM (×3). The combined extracts were evaporated and the residue was diluted with MeOH and loaded on to a SCX cartridge (2 g). The cartridge was eluted with MeOH to wash off the DMSO, then 2N $NH_3$ in MeOH to elute the products. The $NH_3$/MeOH fractions were combined and evaporated. The residue was taken up in MeOH (2 ml) and 4N NaOH (aq, 0.2 ml, 0.8 mmol) was added. The mixture was stirred and heated to 60° C. for 2 hrs. After cooling to RT the MeOH was removed in vacuo and the residue was partitioned between DCM and $H_2O$. 2N HCl (0.5 ml) was added. The pH of the aqueous layer was adjusted to ~7 with $NaHCO_3$ (aq). The aqueous layer was extracted with DCM (×3). The combined extracts were dried ($Na_2SO_4$), filtered and evaporated. The residue was purified by reverse phase HPLC (ABZ+ column) to give the title compound (10 mg) as a colourless solid.

Example 30

{(2S,4R)-1-{(1R)-1-[(Difluoromethoxy)methyl]-4-methylpentyl}-2-[4-(trifluoromethyl)phenyl]piperidin-4-yl}acetic acid

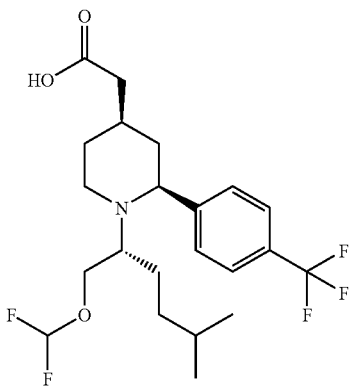 [SMILES: CC(C)CC[C@H](COC(F)F)N1CC[C@@H](CC(=O)O)C[C@H]1c1ccc(C(F)(F)F)cc1]

Step 1: Methyl {(2S,4R)-1-{(1R)-1-[(difluoromethoxy)methyl]-4-methylpentyl}-2-[4-(trifluoromethyl)phenyl]piperidin-4-yl}acetate

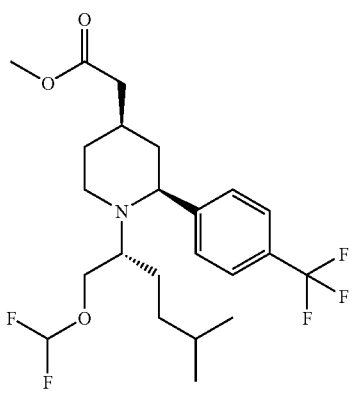 [SMILES: COC(=O)C[C@@H]1CCN([C@H](CCC(C)C)COC(F)F)[C@H](c2ccc(C(F)(F)F)cc2)C1]

2-(Fluorosulphonyl)difluoroacetic acid (0.040 ml, 0.385 mmol) was added to a stirred solution/suspension of methyl {(2S,4R)-1-[(1R)-1-(hydroxymethyl)-4-methylpentyl]-2-[4-(trifluoromethyl)phenyl]piperidin-4-yl}acetate (Example 29, Step 1, 160 mg, 0.385 mmol) and $Na_2SO_4$ (11 mg, 0.077 mmol) in dry $CH_3CN$ (1 ml) at RT under $N_2$. The reaction was then stirred and heated at 50° C. After 2 hours, the reaction was allowed to cool to RT, then partitioned between DCM/$H_2O$. The aqueous layer was extracted with DCM (×2). The combined extracts were dried ($Na_2SO_4$), filtered and evaporated. The residue was purified by chromatography (silica, 4-6-10% EtOAc/isohexanes) to give the title compound (13 mg) as an oil. M/Z 466 ($MH^+$).

Step 2: {(2S,4R)-1-{(1R)-1-[(Difluoromethoxy)methyl]-4-methylpentyl}-2-[4-(trifluoromethyl)phenyl]piperidin-4-yl}acetic acid A solution of LiOH (5 mg, 0.209 mmol) in $H_2O$ (0.5 ml) was added to a stirred solution of the ester (Step 1, 13 mg, 0.028 mmol) in THF (1 ml) at RT. The mixture was stirred at RT for 3 days. 2N HCl (0.5 ml) was added. The pH of the aqueous layer was adjusted to ~7 with NaHCO$_3$ (aq). The aqueous layer was extracted with DCM (×3). The combined extracts were dried (Na$_2$SO$_4$), filtered and evaporated to give the title compound (12 mg) as a colourless solid after evaporation from pentane. M/Z 452 (MH$^+$).

Example 31

{(2S,4R)-1-[(1S,4R)-5-(Benzyloxy)-4-methyl-1-(3, 3,3-trifluoropropyl)pent-2-yn-1-yl]-2-[4-(trifluoromethyl)phenyl]piperidin-4-yl}acetic acid

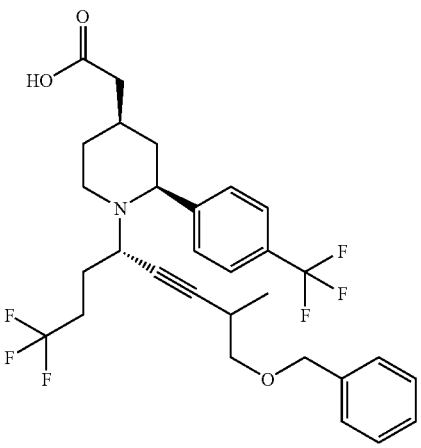 [SMILES: CC(C#C[C@H](CCC(F)(F)F)N1CC[C@@H](CC(=O)O)C[C@H]1c1ccc(C(F)(F)F)cc1)COCc1ccccc1]

Step 1: 3-(Benzyloxy)-2-methylpropanal

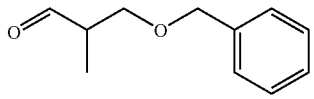

NaH (60% disp., 2.44 g, 61.0 mmol) was added portionwise to a stirred solution of 2-methyl-1,3-propanediol (4.93 ml, 55.5 mmol) in dry THF (180 ml) at 0° C. under N$_2$. The cooling bath was removed after complete addition. The mixture was stirred at RT for 1 hr, then recooled in an ice bath. Benzyl bromide (7.0 ml, 58.9 mmol) was added and the reaction was allowed to warm to RT o/n. The reaction was quenched with saturated aqueous ammonium chloride (150 ml) and diluted with EtOAc (200 ml). The layers were separated and the aqueous layer was extracted with EtOAc (×2). The combined extracts were washed with brine (×1), dried (Na$_2$SO$_4$), filtered and evaporated. The residue was purified by chromatography (silica, 10-50% EtOAc/isohexanes) to give the alcohol (2.43 g) pale yellow oil.

Tetra-n-propyl ammonium perruthenate (VII) (0.234 g, 0.666 mmol) was added to a stirred solution/suspension of the alcohol from above (2.4 g, 13.32 mmol), 4-methylmorpholine N-oxide (1.87 g, 16 mmol) and activated molecular sieves (5 g) in dry DCM (25 ml) at 0° C. under N$_2$. After 5 min, the cooling bath was removed and the reaction was stirred at RT for 3 hours. The mixture was diluted with EtOAc/isohexane (1:1, 100 ml) and then filtered through a pad of silica—eluting with EtOAc/isohexane (1:1, 200 ml). The filtrate was evaporated and the residue was purified by chromatography (silica, 10-20-50% EtOAc/isohexane) to give the aldehyde (1.11 g) colourless liquid.

Step 2: {[(2-Methylbut-3-yn-1-yl)oxy]methyl}benzene

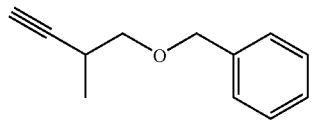

A solution of PPh$_3$ (3.24 g, 12.34 mmol) in dry DCM (10 ml) was added to a stirred solution of carbon tetrabromide (4.09 g, 12.34 mmol) in dry DCM (10 ml) under N$_2$ at −20° C. The orange solution was stirred at −20° C. for 20 minutes, then cooled to −60° C. A solution of 3-(benzyloxy)-2-methylpropanal (1.1 g, 6.17 mmol) and triethylamine (0.860 ml, 6.17 mmol) in dry DCM (5+5 ml) was added such that the internal temperature ~−60° C. The reaction was maintained at this temperature for 30 minutes. The cooling bath was removed and the reaction was allowed to warm to RT and stirred at this temperature O/N. The mixture was concentrated in vacuo to ~⅓ volume, then diluted with isohexanes (~1000 ml). After stirring at RT for 30 min, the solid was removed by filtration. The filtrate was evaporated—some triphenylphosphine oxide had been carried through. The residue was purified by chromatography (silica, 1-3% Et2O/isohexanes) to give the dibromo alkene (1.13 g) as a colourless liquid.

A solution of BuLi (4.32 ml, 6.92 mmol) (1.6M in hexanes) was added dropwise to a stirred solution of the dibromo alkene (above, 1.1 g, 3.29 mmol) in dry THF (15 ml) under N$_2$, such that the internal temperature <−70° C. The reaction was stirred at this temperature for 30 minutes and then quenched with saturated aqueous ammonium chloride (1 ml) before being allowed to warm to RT. The mixture was partitioned between diethyl ether and water. The aqueous layer was extracted with diethyl ether (×2). The combined extracts were washed with brine (×1), dried (Na$_2$SO$_4$), filtered and evaporated. The residue was purified by chromatography (silica, 1-4% Et$_2$O/isohexane) to give the alkyne (0.55 g) as a colourless liquid.

Step 3: Methyl {(2S,4R)-1-[(1S)-5-(benzyloxy)-4-methyl-1-(3,3,3-trifluoropropyl)pent-2-yn-1-yl]-2-[4-(trifluoromethyl)phenyl]piperidin-4-yl}acetate

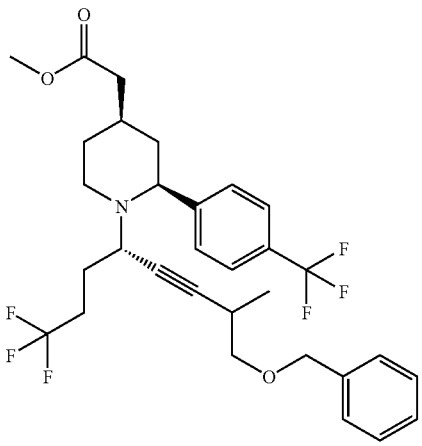 [SMILES: COC(=O)C[C@@H]1CCN([C@H](C#CC(C)COCc2ccccc2)CCC(F)(F)F)[C@H](c2ccc(C(F)(F)F)cc2)C1]

A mixture of (+)-methyl {(2S,4R)-2-[4-(trifluoromethyl)phenyl]piperidin-4-yl}acetate (Intermediate 2, 440 mg, 1.460 mmol), {[(2-methylbut-3-yn-1-yl)oxy]methyl}benzene (509 mg, 2.92 mmol), 4,4,4-trifluorobutyraldehyde (368 mg, 2.92 mmol) and gold(III) bromide (63.8 mg, 0.146 mmol) were combined in water (1.5 ml) in a 5 ml microwave vial. The vial was sealed and the mixture was stirred and heated at 70° C. in the microwave. After cooling to RT, the mixture was diluted with MeOH and then loaded on to a SCX cartridge (2 g). The cartridge was washed with MeOH (5×10 ml), then the product was eluted with 2N NH$_3$ in MeOH (5×10 ml). The NH$_3$/MeOH fractions were combined and evaporated. The residue was partitioned between EtOAc/H$_2$O. The aqueous layer was extracted with EtOAc (×3). The combined extracts were washed with brine (×1), dried (Na$_2$SO$_4$), filtered and evaporated. The residue was purified by chromatography (silica, 5-10% EtOAc/isohexane) to give the title compound (562 mg, mixture of diasteromers) as a colourless oil. M/Z 584 (MH$^+$).

Step 4: {(2S,4R)-1-[(1S,4R)-5-(Benzyloxy)-4-methyl-1-(3,3,3-trifluoropropyl)pent-2-yn-1-yl]-2-[4-(trifluoromethyl)phenyl]piperidin-4-yl}acetic acid A solution of lithium hydroxide (19.7 mg, 0.822 mmol) in water (1 ml) was added to a stirred solution of the ester (Step 3, 96 mg, 0.164 mmol) in THF (2 ml) at RT. The mixture was stirred at RT o/n. 2N HCl (1 ml) was added The pH of the aqueous layer was adjusted to 7 with NaHCO$_3$ (aq). The aqueous layer was extracted with DCM (×3). The combined extracts were dried (Na$_2$SO$_4$), filtered and evaporated. The residue was purified by chromatography (silica, 2-5% MeOH/DCM) to give the acid (91 mg) as a colourless oil. M/Z 570 (MH$^+$).

Example 32

{(2S,4R)-1-[(1R,4R/S)-5-(Benzyloxy)-4-methyl-1-(3,3,3-trifluoropropyl)pentyl]-2-[4-(trifluoromethyl)phenyl]piperidin-4-yl}acetic acid

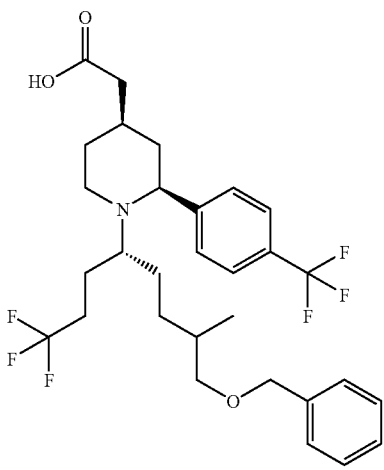 [SMILES: CC(CC[C@H](CCC(F)(F)F)N1CC[C@@H](CC(=O)O)C[C@H]1c1ccc(C(F)(F)F)cc1)COCc1ccccc1]

Step 1: Methyl {(2S,4R)-1-[(1R,4R/S)-5-(benzyloxy)-4-methyl-1-(3,3,3-trifluoropropyl)pentyl]-2-[4-(trifluoromethyl)phenyl]piperidin-4-yl}acetate and Methyl {(2S,4R)-1-[(1R,4R/S)-5-hydroxy-4-methyl-1-(3,3,3-trifluoropropyl)pentyl]-2-[4-(trifluoromethyl)phenyl]piperidin-4-yl}acetate

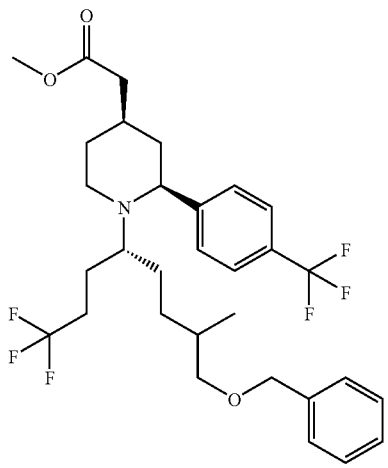

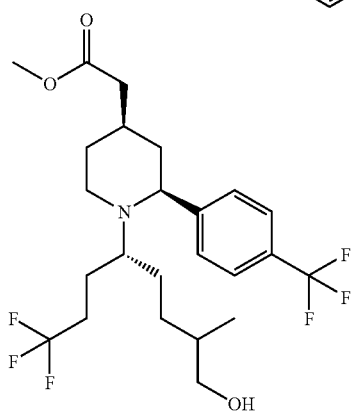

A solution of methyl {(2S,4R)-1-[(1S)-5-(benzyloxy)-4-methyl-1-(3,3,3-trifluoropropyl)pent-2-yn-1-yl]-2-[4-(trifluoromethyl)phenyl]piperidin-4-yl}acetate (Example 31, Step 3, 470 mg, 0.805 mmol) in MeOH (10 ml) was hydrogenated over Raney nickel (~500 mg) on the Parr at 50 psi overnight. MS suggests complete reduction of the alkyne, but only partial removal of the benzyl group. The catalyst was removed by filtration, washing with DCM. The filtrate was evaporated and the residue was partitioned between DCM and H$_2$O. The aqueous layer was extracted with DCM (×3). The combined extracts were dried (Na$_2$SO$_4$), filtered and evaporated. The residue was purified by chromatography (silica, 5-40% EtOAc/isohexane) to give the benzyl ether (212 mg) as a colourless oil, M/Z 588 (MH$^+$); and the alcohol (126 mg) as a colourless oil, M/Z 498 (MH$^+$).

Step 2: {(2S,4R)-1-[(1R,4R/S)-5-(Benzyloxy)-4-methyl-1-(3,3,3-trifluoropropyl)pentyl]-2-[4-(trifluoromethyl)phenyl]piperidin-4-yl}acetic acid A solution of lithium hydroxide (41 mg, 1.702 mmol) in water (1 ml) was added to a stirred solution of methyl {(2S,4R)-1-[(1R,4R/S)-5-(benzyloxy)-4-methyl-1-(3,3,3-trifluoropropyl)pentyl]-2-[4-(trifluoromethyl)phenyl]piperidin-4- yl}acetate (Step 1, 200 mg, 0.340 mmol) in THF (2 ml) at RT. The mixture was stirred at RT o/n. 2N HCl (1 ml) was added The pH of the aqueous layer was adjusted to 7 with NaHCO₃ (aq). The aqueous layer was extracted with DCM (×3). The combined extracts were dried (Na₂SO₄), filtered and evaporated. The residue was purified by chromatography (silica, 2-4% MeOH/DCM) to give the title compound (180 mg) as a colourless foam/M/Z 574 (MH⁺).

Example 33

{(2S,4R)-1-[(1R,4R/S)-5-Hydroxy-4-methyl-1-(3,3,3-trifluoropropyl)pentyl]-2-[4-(trifluoromethyl)phenyl]piperidin-4-yl}acetic acid

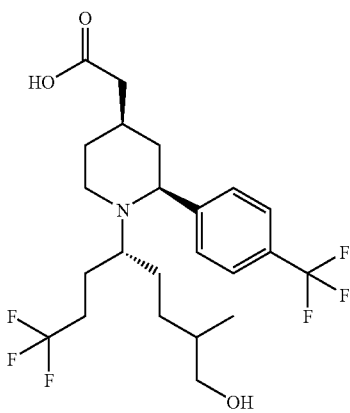 [SMILES: CC(CO)CC[C@H](CCC(F)(F)F)N1CC[C@@H](CC(=O)O)C[C@H]1c1ccc(C(F)(F)F)cc1]

A solution of lithium hydroxide (26.2 mg, 1.095 mmol) in water (1.000 ml) was added to a stirred solution of methyl{(2S,4R)-1-[(1R,4R/S)-5-hydroxy-4-methyl-1-(3,3,3-trifluoropropyl)pentyl]-2-[4-(trifluoromethyl)phenyl]piperidin-4-yl}acetate (Example 32, Step 1, 109 mg, 0.219 mmol) in THF (2 ml) at RT. The mixture was stirred at RT o/n. 2N HCl (1 ml) was added The pH of the aqueous layer was adjusted to 7 with NaHCO₃ (aq). The aqueous layer was extracted with DCM (×3). The combined extracts were dried (Na₂SO₄), filtered and evaporated. The residue was purified by chromatography (silica, 2-4-8% MeOH/DCM) to give the title compound (mixture of diastereomers, 46 mg) as a colourless foam. M/Z 484 (MH⁺).

Example 34

(±){(2S,4R)-1-[(1S-4-methyl-1-(2-methylpropyl) pentyl]-2-[4-(trifluoromethyl)phenyl]piperidin-4-yl}acetic acid

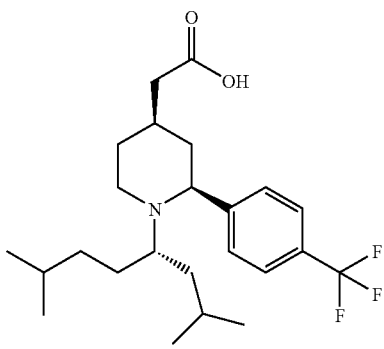 [SMILES: CC(C)CC[C@@H](CC(C)C)N1CC[C@@H](CC(=O)O)C[C@H]1c1ccc(C(F)(F)F)cc1]

Step 1: Methyl{(2S,4R)-1-[(1R)-1-(1H-1,2,3-benzotriazol-1-yl)-4-methylpentyl]-2-[4-(trifluoromethyl)phenyl]piperidin-4-yl}acetate

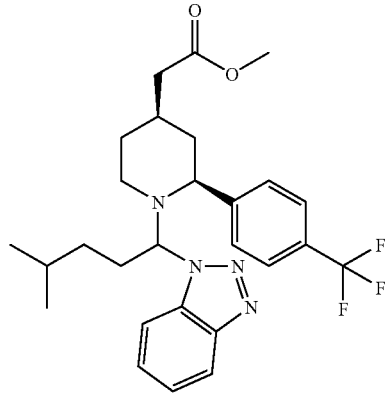 [SMILES: COC(=O)C[C@@H]1CCN(C(CCC(C)C)n2nnc3ccccc32)[C@H](c2ccc(C(F)(F)F)cc2)C1]

A mixture of (±)-methyl{(2S,4R)-2-[4-(trifluoromethyl)phenyl]piperidin-4-yl}acetate (Intermediate 1, 453 mg, 1.5 mmol), 4-methylpentanal (150 mg, 1.5 mmol) and benzotriazole (178.5 mg, 1.5 mmol) were combined in toluene (15 ml) and the reaction was stirred and heated a 150° C. under Dean-Stark conditions for 16 Hrs. The mixture was evaporated in vacuo to provide a pale gum.

Step 2: (±)methyl{(2S,4R)-1-[(1R)-4-methyl-1-(2-methylpropyl)pentyl]-2-[4-(trifluoromethyl)phenyl]piperidin-4-yl}acetate

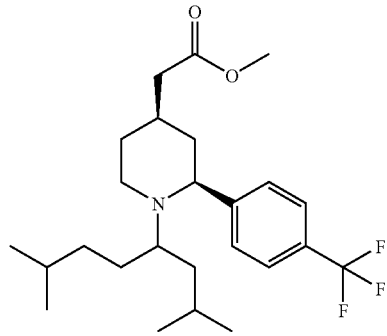 [SMILES: COC(=O)C[C@@H]1CCN(C(CCC(C)C)CC(C)C)[C@H](c2ccc(C(F)(F)F)cc2)C1]

Zinc chloride (1M in Et₂O, 5 ml, 5 mmol) was added slowly to a cold 0° C. solution of isobutyl magnesium bromide (2M in Et₂O, 2.5 ml, 5 mmol) under a nitrogen atmosphere, maintaining the temperature below 0° C. during the addition. Once the addition was complete the mixture was stirred at room temperature for one hour. The white suspension was cooled to 0° C. and the benzotriazole adduct from Step 1 (1.5 mmol) was added slowly as a solution in DCM (5 ml). The cooling was removed and the mixture was stirred at room temperature for 16 hours. The mixture was diluted with NH₄Cl (half sat.) and with DCM and the mixture was filtered though a Celite® bed. The phases were separated and the aqueous extracted with DCM. The extracts were dried (MgSO₄) and evaporated in vacuo to yellow gum which was purified by flash chromatography (silica gel, 5% Et₂O in isohexane) to give the title compound as a single diastereoisomer (48 mg, 22%).

Step 3

A solution of LiOH (12 mg, 0.5 mmol) in H₂O (1 ml) was added to a stirred solution of (±)methyl{(2S,4R)-1-[(1R)-4-methyl-1-(2-methylpropyl)pentyl]-2-[4-(trifluoromethyl)phenyl]piperidin-4-yl}acetate (Step 2, 46 mg, 0.1 mmol) in THF (3 ml) at RT. The mixture was stirred at RT for 18 hrs. HCl (2N) was added and the THF was removed in vacuo. The residue was partitioned between CH₂Cl₂/H₂O. The pH of the aqueous layer was adjusted to ~pH7 with saturated aqueous NaHCO₃. The aqueous layer was extracted with CH₂Cl₂ (×3). The combined extracts were dried (Na₂SO₄) filtered and evaporated. The residue was purified by chromatography (silica, 5% MeOH/CH₂Cl₂) to give the acid (20 mg) as a colourless foam. M/Z (ES⁺) 428 (MH⁺).

Example 35

{(2S,4R)-1-[(1R/S)-4,4,4-trifluoro-1-isobutylbutyl]-2-[4-(trifluoromethyl)phenyl]piperidin-4-yl}acetic acid

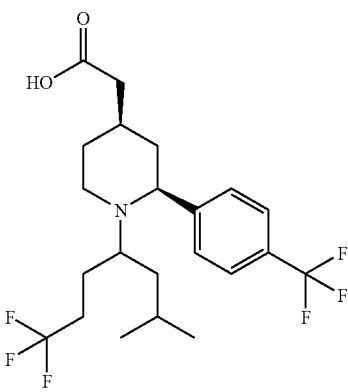 [SMILES: CC(C)CC(CCC(F)(F)F)N1CC[C@@H](CC(=O)O)C[C@H]1c1ccc(C(F)(F)F)cc1]

This analogue was prepared according to the procedures in Example 34, substituting 4,4,4-trifluorobutanal for 4-methylpentanal in Step 1. M/Z 454 (MH⁺).

Example 36

(±)-{4-[4-Methyl-1-(3-methylbutyl)pentyl]-3-[4-(trifluoromethyl)phenyl]piperazin-1-yl}acetic acid

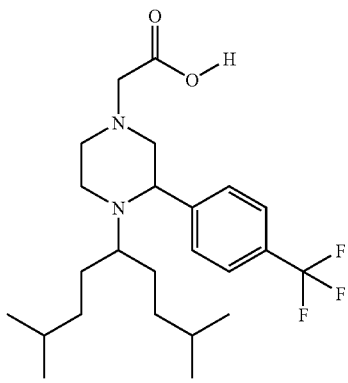 [SMILES: CC(C)CCC(CCC(C)C)N1CCN(CC(=O)O)CC1c1ccc(C(F)(F)F)cc1]

Step 1: 2-[4-(Trifluoromethyl)phenyl]pyrazine

A mixture of chloropyrazine (10, 0.087 mol), 4-(trifluoromethyl)phenylboronic acid (21 g), palladium(diphenylphosphino)ferrocene dichloride (3.5 g, 5 mol %) and sodium carbonate (100mL, 2M) in dioxane (200 mL) was degassed (×3) via Firestone valve. The mixture was heated under reflux for 1 h. Dioxane was removed in vacuo. The residue was dispersed between ethyl acetate and water and the organic phase was washed with brine, dried (MgSO4) and evaporated. The black residue was dry-loaded onto silica and purified by elution with 5-25% ethyl acetate in iso-hexane. This afforded the product as white crystals. ¹H NMR (400 MHz, CDCl₃): δ 7.78 (2H, d, J 8.2), 8.15 (2H, d, J 8.2), 8.59 (1H, d, J 2.5), 8.68 (1H, t, J 2.0), 9.08 (1H, d, J 1.4).

Step 2: (±)-2-[4-(Trifluoromethyl)phenyl]piperazine

The pyrazine described in Step 1 (13 g, 0.058 mol) was dissolved in acetic acid (100 mL) and palladium acetate added. This mixture as hydrogenated at 45 psi for 4 h. The mixture was filtered to remove catalyst and the filtrate was concentrated in vacuo to give the product as brown solid. ¹H NMR (500 MHz, CD₃OD): δ 1.98 (6H, s), 2.93 (1H, t, J 11.9), 3.03-3.15 (2H, m), 3.26-3.32 (3H, m), 4.09 (1H, dd, J 2.7, 11.2), 7.65 (2H, d, J 8.3), 7.72 (2H, d, J 8.2).

Step 3: (±)-Methyl {3-[4-(trifluoromethyl)phenyl]piperazin-1-yl}acetate

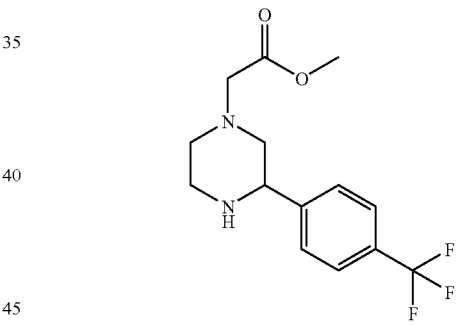

A mixture of the piperazine described in Step 2 above (2.1 g, 9 mmol), methyl bromoacetate (1 mL, 9 mmol) and potassium carbonate (2.4 g, 18 mmol) in acetonitrile (30 mL) was stirred overnight at room temperature. The mixture was filtered, evaporated and purified on silica using 25-50% ethyl acetate in iso-hexane as eluant.

¹H NMR (500 MHz, CDCl₃): δ 2.22 (1H, t, J 10.6), 2.37-2.43 (1H, m), 2.93 (2H, t, J 9.4), 3.10-3.17 (2H, m), 3.26 (2H, s), 3.72 (3H, s), 7.52 (2H, d, J 8.1), 7.58 (2H, d, J 8.2).

Step 3: (±)-{4-[4-Methyl-1-(3-methylbutyl)pentyl]-3-[4-(trifluoromethyl)phenyl]piperazin-1-yl}acetic acid This compound was prepared following the procedure described for Examples 1 & 2 using the compound described in Step 3 above as starting material.

¹H NMR (500 MHz, CD₃OD): δ 0.71-0.82 (1H, m), 0.82-0.91 (12H, m), 0.98-1.13 (3H, m), 1.30-1.48 (5H, m), 1.61-1.72 (1H, m), 2.13-2.23 (1H, m), 2.73 (1H, dt, J 15.1, 2.8), 2.84 (1H, q, J 14.0), 2.88 (1H, dt, J 14.6, 3.0), 3.02 (1H, m), 3.25 (1H, m), 3.41 (2H, d, J 3.3), 3.47-3.50 (1H, m), 4.07 (1H, dd, J 13.5, 3.5).

Example 37

{(2S,4R)-2-[4-(Trifluoromethyl)phenyl]-1-[4,4,4-trifluoro-1-(3,3,3-trifluoropropyl)butyl]piperidin-4-yl}acetic acid

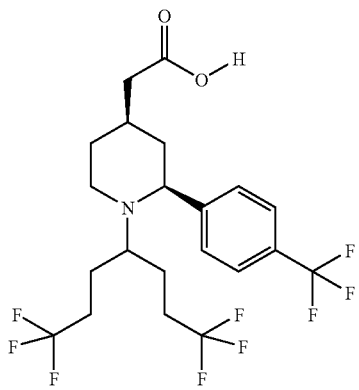 [SMILES: O=C(O)C[C@@H]1CCN(C(CCC(F)(F)F)CCC(F)(F)F)[C@H](c2ccc(C(F)(F)F)cc2)C1]

Step 1: 1,1,1,7,7,7-Hexafluoroheptan-4-ol

3-Bromo-1,1,1-trifluoropropane (31 g, 0.175 mol) was dissolved in THF (175 mL). Mg (4.2 g, 0.175 mol) was placed in a 1 L, 3-necked round-bottom flask equipped with a condenser, nitrogen inlet and thermometer. The bromide solution (10 mL) was added to cover the magnesium and upon stirring a mild exotherm commenced. The temperature was kept <40° C. by immersing the flask in a bowl of water. The bromide was added slowly to maintain this mild exothermic reaction. When the exotherm had subsided the mixture was cooled in ice-water and methyl formate (7 mL, 0.11 mol) in THF (175 mL) was added. The mixture was stirred for 30 min and then quenched with NH$_4$Cl (aq.soln. 100 mL). The mixture was extracted with ethyl acetate. The organic extracts were washed with brine, dried (MgSO$_4$) and evaporated.

$^1$H NMR (400 MHz, CD$_3$Cl): δ 1.61-1.81 (4H, m), 2.10-2.39 (4H, m), 3.69-3.76 (1H, m).

Step 2: 1,1,1,7,7,7-Hexafluoroheptan-4-one 1,1,1,7,7,7-Hexafluoroheptan-4-ol (1.4 g, 6.25 mmol) was dissolved in CH$_2$Cl$_2$ (12 mL) and pyridinium chlorochromate (PCC) (1.48 g, 6.87 mmol) was added. The mixture was stirred for 4 h. Additional PCC (800 mg) was added and the mixture stirred for 1 h. The mixture was filtered through celite and silica, washing with DCM. The resulting pale yellow solution was evaporated at room temperature to afford the title compound.

$^1$H NMR (400 MHz, CD$_3$Cl): δ 2.39-2.49 (4H, m), 2.73 (4H, t, J 7.35).

Step 3: (±)-Methyl {(2S*)-2-[4-(trifluoromethyl)phenyl]-1-[4,4,4-trifluoro-1-(3,3,3-trifluoropropyl)butyl]piperidin-4-yl}acetate Intermediate 2 (301 mg, 1 mmol), 1,1,1,7,7,7-hexafluoroheptan-4-one (500 mg, 2 mmol) and triethylamine (0.8 mL, 6 mmol) were dissolved in CH$_2$Cl$_2$ (4 mL) and the mixture was cooled to −78° C. TiCl$_4$ (2 mL, 1M in CH$_2$Cl$_2$) was added dropwise to give a dark orange mixture. This mixture was allowed to warm to 0° C. for 5 min then re-cooled to −78° C. NaCNBH$_3$ (376 mg, 6 mmol) in methanol (2 mL) was added and the mixture was warmed to room temperature. The mixture was diluted with water and ethyl acetate and was filtered through celite to remove titanium salts. The organic extracts were pooled, washed with brine, dried and evaporated. The residue was purified on silica using 20-50% CH$_2$Cl$_2$ in isohexane as eluant to give the product as a crystalline solid (85 mg, 20%) upon evaporation.

$^1$H NMR (500 MHz, CDCl$_3$): δ 1.24-1.38 (4H, m), 1.43 (4H, m), 1.73-1.99 (6H, m), 2.19-2.31 (4H, m), 2.40-2.54 (1H, m), 2.89 (1H, m), 3.59 (1H, dd, J 11.0, 2.6), 3.65 (3H, s), 7.36 (2H, d, J 7.2), 7.59 (2H, d, J 8.1). MS (ES) m/z 508 (MH$^+$, 100%)

Step 4: {(2S,4R)-2-[4-(Trifluoromethyl)phenyl]-1-[4,4,4-trifluoro-1-(3,3,3-trifluoropropyl)butyl]piperidin-4-yl}acetic acid The ester described in Step 3 above (80 mg) was dissolved in methanol (1 mL) and sodium hydroxide (4N, 0.2 mL) was added. The mixture was heated at 60° C. for 4 h. The cooled mixture was neutralized with HCl (0.5 mL, 2N) and then sodium bicarbonate (2 mL) and the mixture was extracted with CH$_2$Cl$_2$. The solvent was evaporated and the resulting foam was purified on silica using CH$_2$Cl$_2$ in methanol (0-2%) as eluant.

$^1$H NMR (500 MHz, CDCl$_3$): δ 1.29-1.42 (3H, m), 1.48-1.55 (1H, m), 1.60-1.71 (2H, m), 1.78-2.05 (6H, m), 2.18-2.35 (4H, m), 2.45-2.58 (1H, m), 2.96 (1H, dt, J 11.6, 3.3), 3.66 (1H, dd, J 11, 2.5), 7.49 (2H, d, 7.75). MS (ES$^+$) m/z 494 (MH$^+$, 100%)

Example 38

{(2S,4R)-1-[4,4-dimethyl-1-(3,3-dimethylbutyl)pentyl]-2-[4-(trifluoromethyl)phenyl]piperidin-4-yl}acetic acid

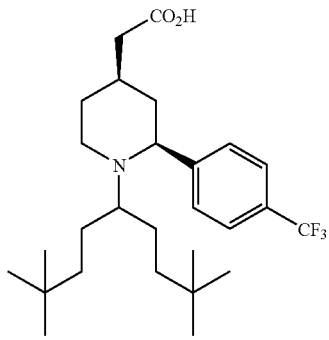 [SMILES: CC(C)(C)CCC(CCC(C)(C)C)N1CC[C@@H](CC(=O)O)C[C@H]1c1ccc(C(F)(F)F)cc1]

Step 1: Ethyl 4,4-dimethylpent-2-enoate

Triethyl phosphonoacetate (17.9 ml, 0.09 mol) was added cautiously over 15 min to a suspension of sodium hydride (60% in oil; 4.4 g, 0.11 mol) in toluene (150 ml). After stirring for a further 45 min, pivaldehyde (11.0 ml, 0.1 mol) was added to the yellow solution and the mixture stirred for 5 h. To the resulting resinous mass was added water (100 ml) followed by citric acid (10%, 50 ml) and the mixture stirred until the appearance of two separate, liquid phases. The organic layer was separated, washed with brine (50 ml), dried (MgSO$_4$) and evaporated to leave the crude product as a yellow oil (13.54 g, 95%). 1H NMR (400 MHz, CDCl$_3$): δ 1.08 (9H, s), 1.29 (3H, t, J 7.1), 4.19 (2H, q, J 7.1), 5.73 (1H, d, J 15.9), 6.97 (1H, d, J 15.9).

Step 2: Ethyl 4,4-dimethylpentanoate

The product from the previous step (13.5 g, 86 mmol) and platinum oxide (195 mg) were shaken in EtOAc (150 ml) under an atmosphere of hydrogen at 20-40 psi for 4 h, after which more platinum oxide (90 mg) was added and hydrogenation at 40 psi resumed for 7 h. The suspension was filtered and the filtrate evaporated to give the crude product as a colourless oil (12.3 g). 1H NMR (400 MHz, CDCl$_3$): δ 0.90 (9H, s), 1.26 (3H, t, J 7.2), 1.53-1.57 (2H, m), 2.25-2.29 (2H, m), 4.12 (2H, q, J 7.2).

Step 3: 4,4-Dimethylpentanol

A solution of lithium aluminium hydride in Et$_2$O (1M; 30 ml) was added to the product from step 2 (6.7 g (42 mmol) in Et$_2$O (75 ml) at a rate to maintain reflux. The solution was stirred overnight at room temperature, then quenched with HCl (5M; 25 ml). The mixture was stirred until all of the solids had dissolved, the organic layer separated, dried (MgSO$_4$) and evaporated. The residual oil was chromatographed on silica gel (2:1 hexanes/EtOAc) to afford the product as a colourless oil (3.51 g). 1H NMR (400 MHz, CDCl$_3$): δ 0.89 (9H, s), 1.20-1.24 (2H, m), 1.43 (1H, br. s), 1.52-1.57 (2H, m), 3.63 (2H, t, J 6.7).

Step 4: 4,4-Dimethylpentanal

PCC (2.36, 11 mmol) was added to a solution of the preceding alcohol (1.0 g, 8.6 mmol) in CH$_2$Cl$_2$ (30 ml) and the mixture stirred for 4 h before diluting with Et$_2$O (100 ml). The suspension was passed through a plug of silica gel and the eluant evaporated cautiously to give a 2:1 mixture of the desired aldehyde and Et$_2$O (755 mg, 57%). 1H NMR (400 MHz, CDCl$_3$): δ 0.84 (9H, s), 1.44-1.48 (2H, m), 2.31-2.35 (2H, m), 9.71 (1H, s).

Step 5: Methyl {(2S,4R)-1-[(S)-1-(3,3-dimethylbutyl)-4,4-dimethylpent-2-yn-1-yl]-2-[4-(trifluoromethyl)phenyl]piperidin-4-yl}acetate

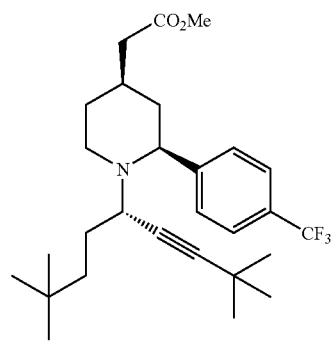 [SMILES: COC(=O)C[C@@H]1CCN([C@H](C#CC(C)(C)C)CCC(C)(C)C)[C@H](c2ccc(C(F)(F)F)cc2)C1]

The preceding aldehyde/Et$_2$O mixture (560 mg, ~3.7 mmol), 3,3-dimethylbut-1-yne (0.6 ml, 5 mmol), Intermediate 2, and gold bromide (57 mg, 0.2 mmol) were combined in water (2 ml) and the mixture subjected to microwave irradiation at 70° C. for 0.5 h. The reaction was partitioned between EtOAc (10 ml) and water (5 ml), the organic layer dried (MgSO$_4$), evaporated, and the residue subjected to chromatography on silica gel (7.5% EtOAc in hexane) to afford the desired product as a yellow oil (897 mg, 92%). 1H NMR (500 MHz, CDCl$_3$): δ 0.83 (9H, s), 1.07-1.01 (1H, m), 1.15-1.41 (4H, m), 1.24 (9H, s), 1.49-1.41 (2H, m), 1.76 (1H, dd, J 12.8, 2.7), 1.83 (1H, d, J 12.8), 1.95-1.88 (1H, m), 2.28-2.18 (2H, m), 2.39 (1H, t, J 10.9), 2.88-2.92 (1H, m), 2.98 (1H, t, J 7.5), 3.47 (1H, dd, J 11.3, 2.4), 3.65 (3H, s), 7.43 (2H, d, J 7.4), 7.55 (2H, d, J 7.4).

Step 6: Methyl{(2S,4R)-1-[4,4-dimethyl-1-(3,3-dimethylbutyl)pentyl]-2-[4-(trifluoromethyl)phenyl]piperidin-4-yl}acetate

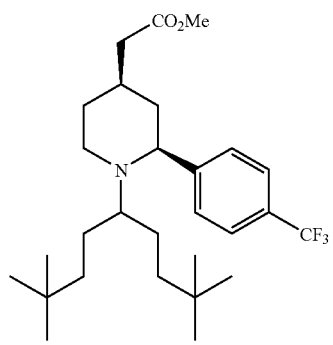

A sample (740 mg) of the product from Step 5 was subjected to hydrogenation under the conditions described in Example 5 Step 1. Isolation of the product provided the Z-olefin as a colourless gum (422 mg). This was resubjected to hydrogenation as before to give, after chromatography on silica gel (5% EtOAc in hexane), the desired product as a gum (245 mg, 33%). 1H NMR (400 MHz, CDCl$_3$): δ 0.63-0.55 (1H, m), 0.80-1.01 (3H, m), 0.82 (9H, s), 0.85 (9H, s), 1.34-1.18 (4H, m), 1.46-1.60 (2H, m), 1.75 (2H, t, J 10.8), 1.89-1.93 (1H, m), 2.05 (1H, t, J 7.3), 2.16-2.28 (3H, m), 2.92 (1H, d, J 11.6), 3.59 (1H, d, J 8.6), 3.64 (3H, s), 7.39 (2H, d, J 7.2), 7.54 (2H, d, J 7.2).

Step 7: {(2S,4R)-1-[4,4-dimethyl-1-(3,3-dimethylbutyl)pentyl]-2-[4-(trifluoromethyl)phenyl]piperidin-4-yl}acetic acid The product from the previous step (240 mg) was subjected to the conditions described in Example 3 to give the title compound as a colourless foam (195 mg). $^1$H NMR (400 MHz, CD$_3$OD): δ 0.59-0.65 (1H, m), 0.86 (9H, s), 0.87 (9H, s), 0.86-1.13 (3H, m), 1.31-1.55 (5H, m), 1.67-1.73 (1H, m), 1.88 (2H, t, J 14.2), 1.92-2.01 (1H, m), 2.15-2.25 (3H, m), 2.50 (1H, t, J 11.7), 3.14 (1H, d, J 11.7), 3.88 (1H, d, J 10.0), 7.52 (2H, d, J 7.8), 7.65 (2H, d, J 8.2); M/Z (ES$^+$) 470 (MH$^+$).

Example 39

{(2S,4R)-1-[(1R)-1-(2-cyclopropylethyl)-4,4,4-trifluorobutyl]-2-[4-(trifluoromethyl)phenyl]-4-piperidinyl}acetic acid

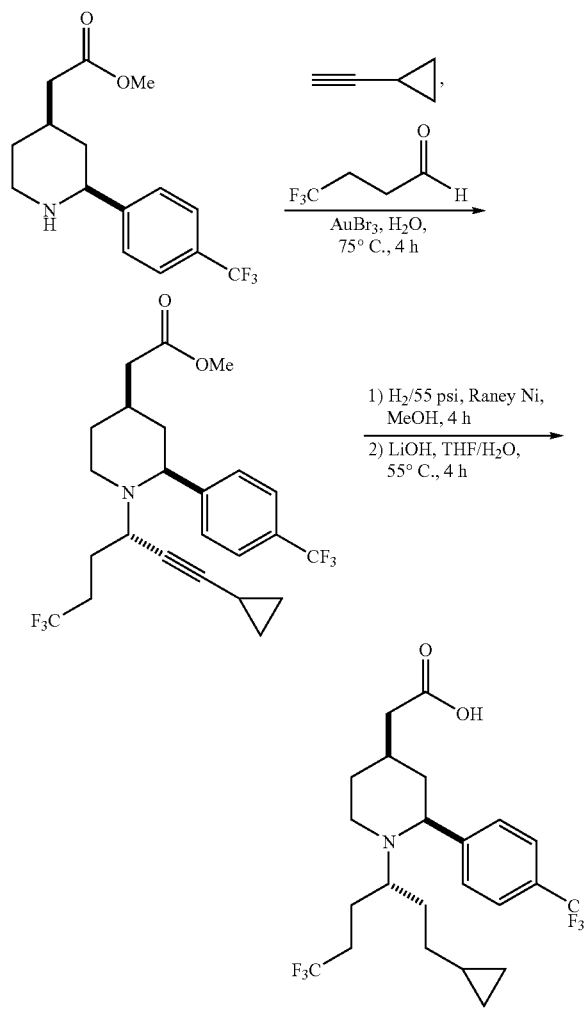

Step 1

A solution of Intermediate 2 (1.00 g, 3.32 mmol), 4,4,4-trifluorobutyraldehyde (837 mg, 6.64 mmol), ethynylcyclopropane (627 mg, 6.64 mmol), and AuBr$_3$ (290 mg, 0.66 mmol) in H$_2$O (4.0 mL) was heated at 75° C. for 4 h. The reaction mixture was concentrated, taken up in CH$_2$Cl$_2$ (2 mL), and purified by flash chromatography (2-50% EtOAc/hexanes) to give 1.2 g (76%) of the desired piperidinyl acetylene methyl ester as a colorless oil confirmed by MS (ESI+): cal'd [M+H]$^+$ 476.2, exp. 476.3.

Step 2

To a solution of the piperidinyl acetylene methyl ester (1.00 g, 2.10 mmol) in MeOH (5 mL) was added slurry 2800 Raney nickel (~500 mg). After 4 h under 55 psi H$_2$, the reaction mixture was filtered over Celite and concentrated. The crude oil was purified by flash chromatography (5-50% EtOAc/hexanes) to give 726 mg (72%) of the saturated piperidine methyl ester as a colorless oil confirmed by MS (ESI+): cal'd [M+H]$^+$ 480.2, exp. 480.1.

Step 3

To a solution of LiOH (125 mg, 5.21 mmol) in H$_2$O (1.5 mL) was added the saturated piperidine methyl ester (500 mg, 1.04 mmol) in THF (1.5 mL) dropwise. After 4 h at 55° C., the reaction mixture was diluted with CH$_2$Cl$_2$ (10 mL) and treated with 1N HCl (15 mL). The layers were separated and the aqueous layer was further extracted with CH$_2$Cl$_2$ (2×10 mL). The combined organics were dried over Na$_2$SO$_4$, filtered, and concentrated. The crude solid was recrystallized from Et$_2$O to give 422 mg (87%) of {(2S,4R)-1-[(1R)-1-(2-cyclopropylethyl)-4,4,4-trifluorobutyl]-2-[4-(trifluoromethyl)phenyl]-4-piperidinyl}acetic acid as a white powder confirmed by MS (ESI+): cal'd [M+H]$^+$ 466.2, exp. 466.2.

Example 40

{(2S,4R)-1-[(1R)-4-methyl-1-(3,3,3-trifluoropropyl)-4-penten-1-yl]-2-[4-(trifluoromethyl)phenyl]-4-piperidinyl}acetic acid

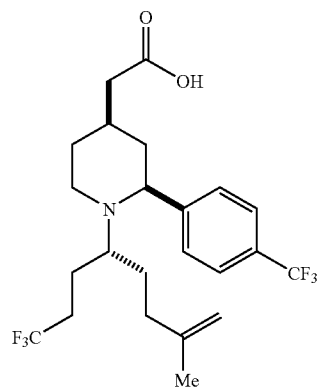

Prepared in similar manner to Example 39, using 2-methyl-1-buten-3-yne in Step 1 MS (ESI+): cal'd [M+H]$^+$ 466.2, exp. 466.1.

Example 41

{(2S,4R)-1-{(1R)-1-[2-(1-cyclohexen-1-yl)ethyl]-4,4,4-trifluorobutyl}-2-[4-(trifluoromethyl)phenyl]-4-piperidinyl}acetic acid

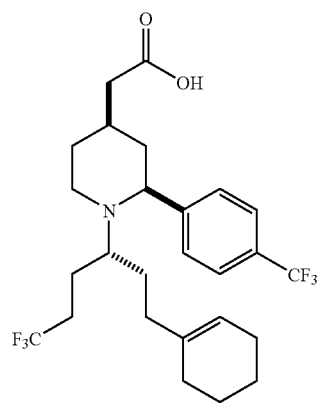

Prepared in similar manner to Example 39, using 1-ethynylcyclohexene in Step 1. The hydrogenation in Step 2 was carried out for 1 hour at 50 psi.

MS (ESI+): cal'd [M+H]$^+$ 506.2, exp. 506.2.

Example 42

{(2S,4R)-1-[(1R)-1-(2-cyclohexylethyl)-4,4,4-trifluorobutyl]-2-[4-(trifluoromethyl)phenyl]-4-piperidinyl}acetic acid

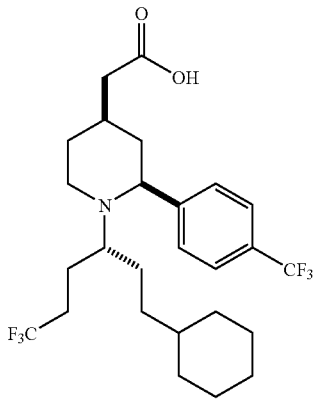

To a solution of methyl{(2S,4R)-1-[(1R)-1-(2-cyclohex-1-en-1-ylethyl)-4,4,4-trifluorobutyl]-2-[4-(trifluoromethyl)phenyl]piperidin-4-yl}acetate (Example 41) (1.00 g, 1.94 mmol) in ETOH (5 mL) was added slurry 2800 Raney nickel (~500 mg). The reaction mixture was shaken under 60 psi $H_2$ for 6 hours. The reaction mixture was then filtered over Celite (25 mL $CH_2Cl_2$ followed by 25 mL MeOH) and concentrated. The crude oil was purified by flash chromatography (10-50% EtOAc/hexanes) to give 561 mg (55%) of the fully saturated piperidine methyl ester confirmed by MS (ESI+): cal'd $[M+H]^+$ 522.3, exp. 522.2.

To a solution of LiOH (92 mg, 3.83 mmol) in $H_2O$ (1 mL) was added methyl{(2S,4R)-1-[(1R)-1-(2-cyclohexylethyl)-4,4,4-trifluorobutyl]-2-[4-(trifluoromethyl)phenyl]piperidin-4-yl}acetate (400 mg, 0.78 mmol) in THF (1 mL) dropwise. After 5 h at 55° C., the reaction mixture was cooled to RT, diluted with $CH_2Cl_2$ (5 mL) and treated with 1N HCl (10 mL). After 15 minutes of stirring at RT, the layers were separated and the aqueous layer further extracted with $CH_2Cl_2$ (210 mL). The combined organics were dried over $Na_2SO_4$, filtered, and concentrated to give 278 mg (71%) of methyl{(2S,4R)-1-[(1R)-1-(2-cyclohexylethyl)-4,4,4-trifluorobutyl]-2-[4-(trifluoromethyl)phenyl]piperidin-4-yl}acetic acid confirmed by MS (ESI⁺): cal'd $[M+H]^+$ 508.3, exp. 508.3.

Example 43

{(2S,4R)-1-{(1R)-4,4,4-trifluoro-1-[2-(1-hydroxycyclopentyl)ethyl]butyl}-2-[4-(trifluoromethyl)phenyl]-4-piperidinyl}acetic acid

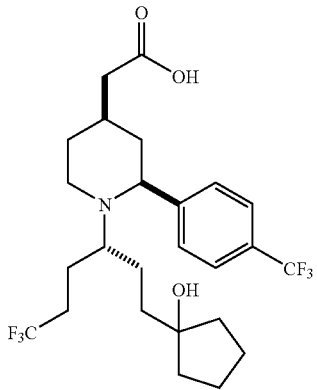 [SMILES: O=C(O)C[C@@H]1CCN([C@@H](CCC(F)(F)F)CCC2(O)CCCC2)[C@H](c2ccc(C(F)(F)F)cc2)C1]

Prepared in similar manner to Example 39, using 1-ethynylcyclopentanol in Step 1. Heating in Step 1 was continued for 48 hours with an additional charge of $AuBr_3$ after 28.5 hours. Hydrogenation in Step 2 was carried out for 2 hr at 50 psi.

MS (ESI⁺): cal'd $[M+H]^+$ 510.2, exp. 510.1.

Example 44

{(2S,4R)-1-{(1R)-4,4,4-trifluoro-1-[2-(1-hydroxycyclohexyl)ethyl]butyl}-2-[4-(trifluoromethyl)phenyl]-4-piperidinyl}acetic acid

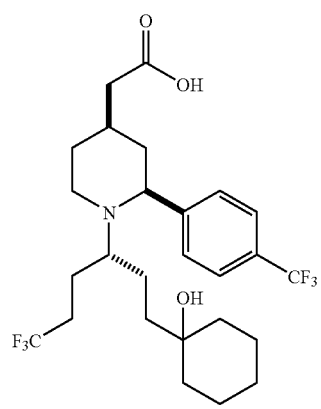 [SMILES: O=C(O)C[C@@H]1CCN([C@@H](CCC(F)(F)F)CCC2(O)CCCCC2)[C@H](c2ccc(C(F)(F)F)cc2)C1]

Prepared in similar manner to Example 39, using 1-ethynyl-1-cyclohexanol in Step 1. Heating in Step 1 was continued for 24 hours with an additional charge of $AuBr_3$ after 4.5 hours. Hydrogenation in Step 2 was carried out for 2.5 hr at 50 psi.

MS (ESI+): cal'd $[M+H]^+$ 524.3, exp. 524.2.

Example 45

{(2S,4R)-2-[4-(trifluoromethyl)phenyl]-1-{(1R)-4,4,4-trifluoro-1-(2-phenylethyl)butyl]-4-piperidinyl}acetic acid

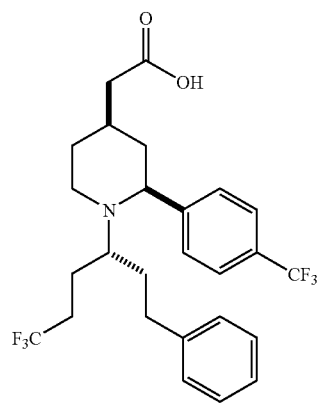 [SMILES: O=C(O)C[C@@H]1CCN([C@H](CCc2ccccc2)CCC(F)(F)F)[C@H](c2ccc(C(F)(F)F)cc2)C1]

Prepared in similar manner to Example 39, using phenylacetylene in Step 1.

MS (ESI+): cal'd $[M+H]^+$ 502.2, exp. 502.1.

Example 46

{(2S,4R)-1-{(1R)-4,4,4-trifluoro-1-[2-(3-fluorophenyl)ethyl]butyl}-2-[4-(trifluoromethyl)phenyl]-4-piperidinyl}acetic acid

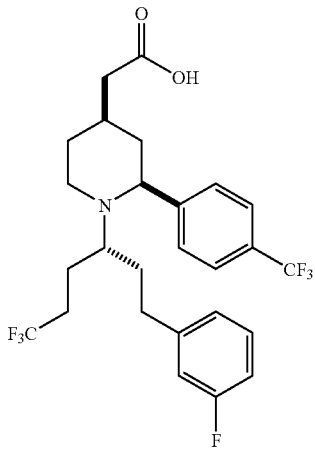 [SMILES: O=C(O)C[C@@H]1CCN([C@H](CCc2cccc(F)c2)CCC(F)(F)F)[C@H](c2ccc(C(F)(F)F)cc2)C1]

Prepared in similar manner to Example 39, using 1-ethynyl-3-fluorobenzene in Step 1.

MS (ESI+): cal'd [M+H]$^+$ 520.2, exp. 520.1.

Example 47

{(2S,4R)-2-[4-(trifluoromethyl)phenyl]-1-{(1R)-4,4,4-trifluoro-1-[2-(3-methylphenyl)ethyl]butyl}-4-piperidinyl}acetic acid

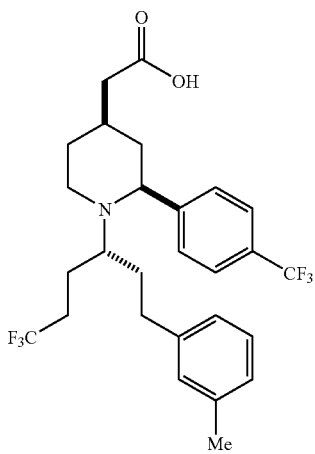 [SMILES: Cc1cccc(CC[C@H](CCC(F)(F)F)N2CC[C@@H](CC(=O)O)C[C@H]2c2ccc(C(F)(F)F)cc2)c1]

Prepared in similar manner to Example 39, using 3-ethynyltoluene in Step 1.

MS (ESI+): cal'd [M+H]$^+$ 516.2, exp. 516.1.

Example 48

[(2S,4R)-2-[4-(trifluoromethyl)phenyl]-1-{(1R)-4,4,4-trifluoro-1-{2-[3-(trifluoromethyl)phenyl]ethyl}butyl)-4-piperidinyl]acetic acid

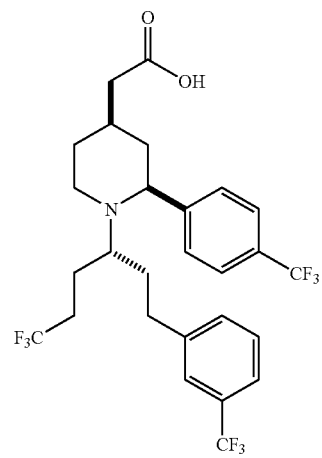 [SMILES: O=C(O)C[C@@H]1CCN([C@H](CCc2cccc(C(F)(F)F)c2)CCC(F)(F)F)[C@H](c2ccc(C(F)(F)F)cc2)C1]

Prepared in similar manner to Example 39, using 3-ethynyl-α,α,α-trifluorotoluene in Step 1.

MS (ESI+): cal'd [M+H]$^+$ 570.2, exp. 570.1.

Example 49

{(2S,4R)-1-{(1R)-1-[2-(4-t-butylphenyl)ethyl]-4,4,4-trifluorobutyl}-2-[4-(trifluoromethyl)phenyl]-4-piperidinyl}acetic acid

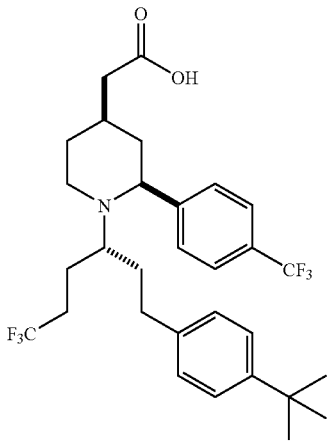 [SMILES: CC(C)(C)c1ccc(CC[C@H](CCC(F)(F)F)N2CC[C@@H](CC(=O)O)C[C@H]2c2ccc(C(F)(F)F)cc2)cc1]

Prepared in similar manner to Example 39, using 4-t-butylphenylacetylene in Step 1. Heating in Step 1 was continued for 23 hours, and the final product was crystallized from pentane.

MS (ESI+): cal'd [M+H]$^+$ 558.3, exp. 558.2.

Example 50

[(2S,4R)-2-[4-(trifluoromethyl)phenyl]-1-{(1R)-4,4,4-trifluoro-1-{2-[4-(trifluoromethyl)phenyl]ethyl}butyl)-4-piperidinyl]acetic acid

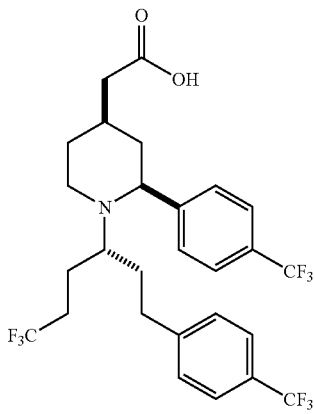 [SMILES: O=C(O)C[C@@H]1CCN([C@H](CCc2ccc(C(F)(F)F)cc2)CCC(F)(F)F)[C@H](c2ccc(C(F)(F)F)cc2)C1]

Prepared in similar manner to Example 39, using 4-ethynyl-α,α,α-trifluorotoluene in Step 1.

MS (ESI+): cal'd [M+H]+ 570.2, exp. 570.1.

Example 51

{(2S,4R)-1-[(1R)-1-[2-(3,5-difluorophenyl)ethyl]-4,4,4-trifluorobutyl}-2-[4-(trifluoromethyl)phenyl]-4-piperidinyl]acetic acid

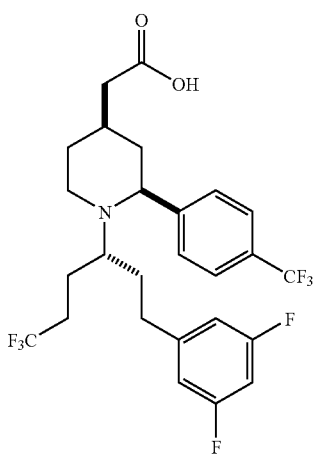 [SMILES: O=C(O)C[C@@H]1CCN([C@H](CCc2cc(F)cc(F)c2)CCC(F)(F)F)[C@H](c2ccc(C(F)(F)F)cc2)C1]

Prepared in similar manner to Example 39, using 1-ethynyl-3,5-difluorobenzene in Step 1.

MS (ESI+): cal'd [M+H]+ 538.2, exp. 538.1.

Example 52

{(2S,4R)-1-[(1R)-1-[2-(2,4-difluorophenyl)ethyl]-4,4,4-trifluorobutyl}-2-[4-(trifluoromethyl)phenyl]-4-piperidinyl}acetic acid

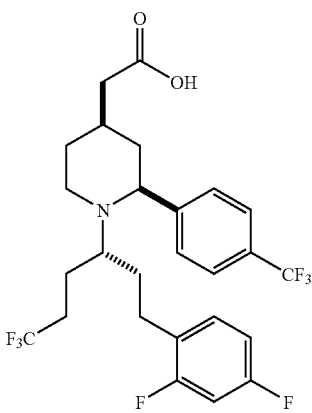 [SMILES: O=C(O)C[C@@H]1CCN([C@H](CCc2ccc(F)cc2F)CCC(F)(F)F)[C@H](c2ccc(C(F)(F)F)cc2)C1]

Prepared in similar manner to Example 39, using 1-ethynyl-2,4-difluorobenzene in Step 1. Hydrogenation in Step 2 was carried out for 12 hours at 55 psi.

MS (ESI+): cal'd [M+H]+ 538.2, exp. 538.1.

Examples 53 and 54

Examples 53 and 54 were prepared by analogous procedures to Example 39, using Intermediate 1(a) and the appropriate alkyne in Step 1:

| Example | Structure | Name | M/Z ES+ [MH]+ |
|---|---|---|---|
| 53 | 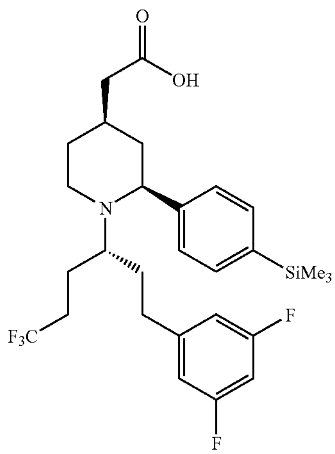 [SMILES: C[Si](C)(C)c1ccc([C@@H]2C[C@H](CC(=O)O)CCN2[C@H](CCc2cc(F)cc(F)c2)CCC(F)(F)F)cc1] | (±)-{1-{1-[2-(3,5-difluorophenyl)ethyl]-4,4,4-trifluorobutyl}-2-[4-(trimethylsilyl)phenyl]piperidin-4-yl}acetic acid | 542.1 |
| 54 | 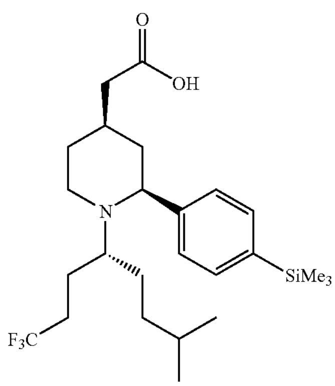 [SMILES: CC(C)CC[C@H](CCC(F)(F)F)N1CC[C@@H](CC(=O)O)C[C@H]1c1ccc([Si](C)(C)C)cc1] | (±)-{1-[4-methyl-1-(3,3,3-trifluoropropyl)pentyl]-2-[4-(trimethylsilyl)phenyl]piperidin-4-yl}acetic acid | 472.1 |

Examples 55-58

Examples 55-58 were prepared by analogous procedures to Example 39 using Intermediate 1(b) and the appropriate aldehyde and alkyne in Step 1:

| Example | Structure | Name | M/Z ES+ [MH]+ |
|---|---|---|---|
| 55 | 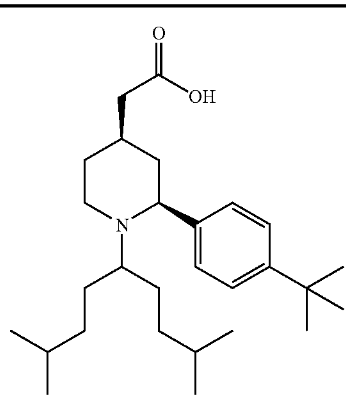 | (±)-{2-(4-tert-butylphenyl)-1-[4-methyl-1-(3-methylbutyl)pentyl]piperidin-4-yl}acetic acid | 430.3 |

-continued

| Example | Structure | Name | M/Z ES+ [MH]+ |
|---------|-----------|------|---------------|
| 56 | 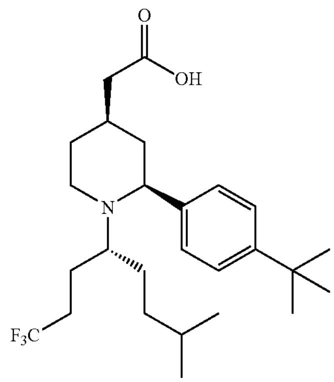 [SMILES: CC(C)CC[C@H](CCC(F)(F)F)N1CC[C@@H](CC(=O)O)C[C@H]1c1ccc(C(C)(C)C)cc1] | (±)-{2-(4-tert-butylphenyl)-1-[4-methyl-1-(3,3,3-trifluoropropyl)pentyl]piperidin-4-yl}acetic acid | 456.2 |
| 57 | 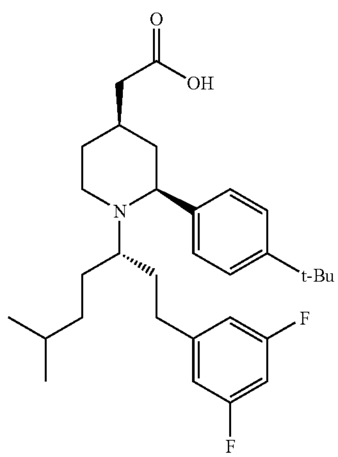 [SMILES: CC(C)CC[C@@H](CCc1cc(F)cc(F)c1)N1CC[C@@H](CC(=O)O)C[C@H]1c1ccc(C(C)(C)C)cc1] | (2-(4-tert-butylphenyl)-1-{1-[2-(3,5-difluorophenyl)ethyl]-4-methylpentyl}piperidin-4-yl)acetic acid | 500.2 |
| 58 | 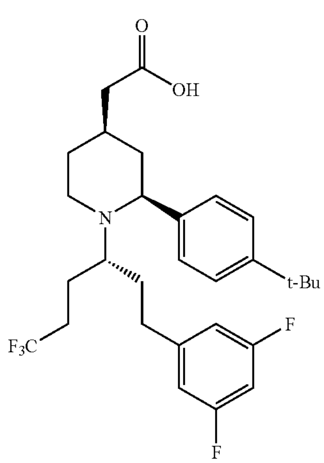 [SMILES: CC(C)(C)c1ccc([C@@H]2C[C@H](CC(=O)O)CCN2[C@H](CCc2cc(F)cc(F)c2)CCC(F)(F)F)cc1] | (2-(4-tert-butylphenyl)-1-{1-[2-(3,5-difluorophenyl)ethyl]-4,4,4-trifluorobutyl}piperidin-4-yl)acetic acid | 526.1 |

Examples 59-65

Examples 59-65 were prepared by analogous procedures to Example 39 using Intermediate 1(c) and the appropriate aldehyde and alkyne in Step 1. In the case of Example 64, Step 2 was omitted:

| Example | Structure | Name | M/Z ES+ [MH]+ |
|---|---|---|---|
| 59 | 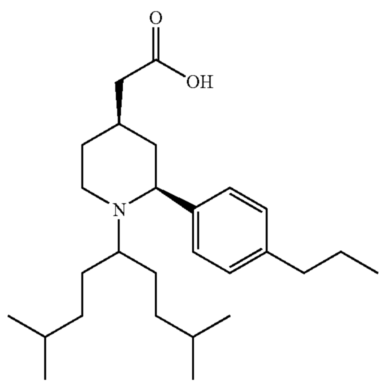 [SMILES: CCCc1ccc([C@@H]2C[C@H](CC(=O)O)CCN2C(CCC(C)C)CCC(C)C)cc1] | (±)-[1-[4-methyl-1-(3-methylbutyl)pentyl]-2-(4-propylphenyl)piperidin-4-yl]acetic acid | 416.3 |
| 60 | 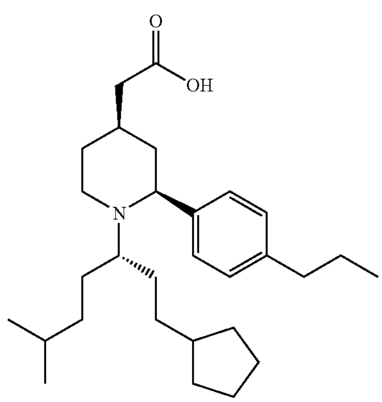 [SMILES: CCCc1ccc([C@@H]2C[C@H](CC(=O)O)CCN2[C@@H](CCC(C)C)CCC2CCCC2)cc1] | (±)-[1-[1-(2-cyclopentylethyl)-4-methylpentyl]-2-(4-propylphenyl)piperidin-4-yl]acetic acid | 442.3 |
| 61 | 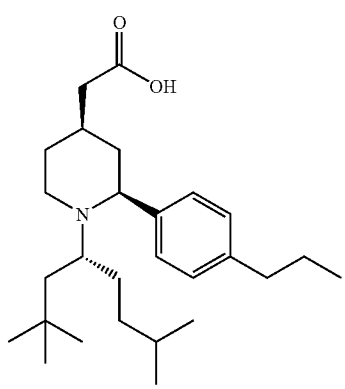 [SMILES: CCCc1ccc([C@@H]2C[C@H](CC(=O)O)CCN2[C@H](CCC(C)C)CC(C)(C)C)cc1] | (±)-[1-[1-(2,2-dimethylpropyl)-4-methylpentyl]-2-(4-propylphenyl)piperidin-4-yl]acetic acid | 416.3 |

| Example | Structure | Name | M/Z ES+ [MH]+ |
|---|---|---|---|
| 62 | 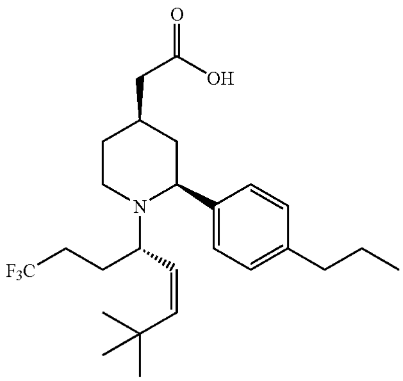 [SMILES: CCCc1ccc([C@@H]2C[C@H](CC(=O)O)CCN2[C@H](/C=C\C(C)(C)C)CCC(F)(F)F)cc1] | (±)-[1-[(2Z)-4,4-dimethyl-1-(3,3,3-trifluoropropyl)pent-2-en-1-yl]-2-(4-propylphenyl)piperidin-4-yl]acetic acid | 454.3 |
| 63 | 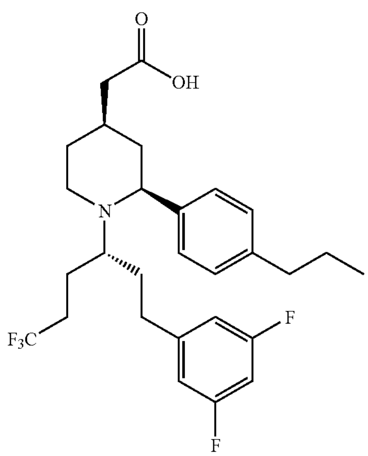 [SMILES: CCCc1ccc([C@@H]2C[C@H](CC(=O)O)CCN2[C@H](CCc2cc(F)cc(F)c2)CCC(F)(F)F)cc1] | (±)-[1-{1-[2-(3,5-difluorophenyl)ethyl]-4,4,4-trifluorobutyl}-2-(4-propylphenyl)piperidin-4-yl]acetic acid | 512.1 |
| 64 | 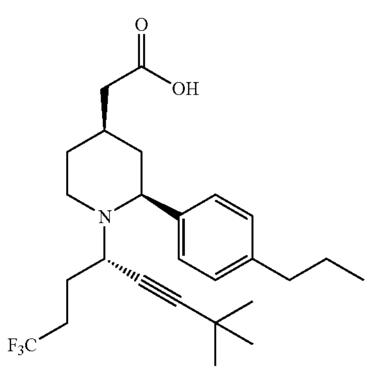 [SMILES: CCCc1ccc([C@@H]2C[C@H](CC(=O)O)CCN2[C@H](C#CC(C)(C)C)CCC(F)(F)F)cc1] | (±)-[1-[4,4-dimethyl-1-(3,3,3-trifluoropropyl)pent-2-yn-1-yl]-2-(4-propylphenyl)piperidin-4-yl]acetic acid | 452.3 |

Examples 65 and 66

Examples 65 and 66 were prepared by analogous procedures to Example 39 using Intermediate 1(d) and the appropriate alkyne in Step 1:

| Example | Structure | Name | M/Z ES+ [MH]+ |
|---|---|---|---|
| 65 | 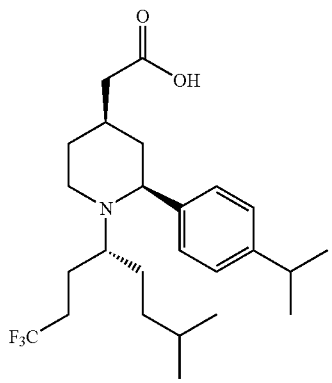 [SMILES: CC(C)CC[C@H](CCC(F)(F)F)N1CC[C@@H](CC(=O)O)C[C@H]1c1ccc(C(C)C)cc1] | (±)-{2-(4-isopropylphenyl)-1-[4-methyl-1-(3,3,3-trifluoropropyl)pentyl]piperidin-4-yl}acetic acid | 442.2 |
| 66 | 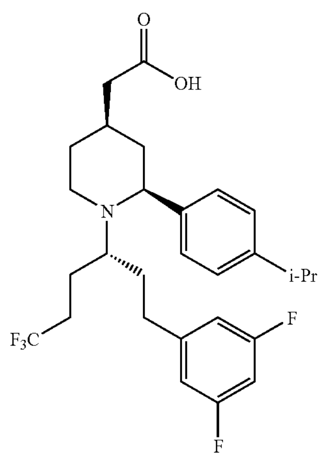 [SMILES: CC(C)c1ccc([C@@H]2C[C@H](CC(=O)O)CCN2[C@H](CCc2cc(F)cc(F)c2)CCC(F)(F)F)cc1] | (±)-[1-{1-[2-(3,5-difluorophenyl)ethyl]-4,4,4-trifluorobutyl}-2-(4-isopropylphenyl)piperidin-4-yl]acetic acid | 512.1 |

Examples 67 and 68

Examples 67 and 68 were prepared by analogous procedures to Example 39 using Intermediate 1(e) and the appropriate aldehyde and alkyne in Step 1:

| Example | Structure | Name | M/Z ES+ [MH]+ |
|---|---|---|---|
| 67 | 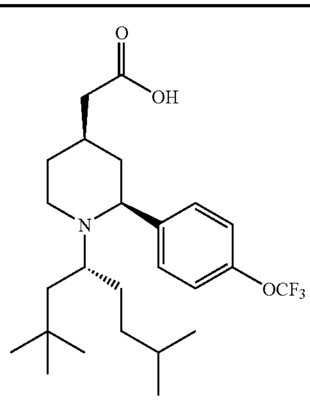 | (±)-{1-[1-(2,2-dimethylpropyl)-4-methylpentyl]-2-[4-(trifluoromethoxy)phenyl]piperidin-4-yl}acetic acid | 458.2 |

| Example | Structure | Name | M/Z ES+ [MH]+ |
|---|---|---|---|
| 68 | 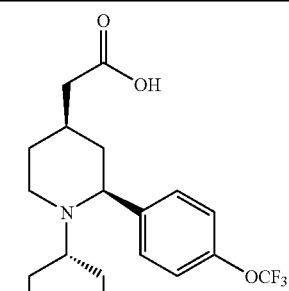 | (±)-{1-[4-methyl-1-(3,3,3-trifluoropropyl)pentyl]-2-[4-(trifluoromethoxy)phenyl]piperidin-4-yl}acetic acid | 484.1 |

Example 69

{(2S,3R)-1-[(1R)-4,4-dimethyl-1-(3,3,3-trifluoropropyl)pentyl]-2-[4-(trifluoromethyl)phenyl]piperidin-3-yl}acetic acid

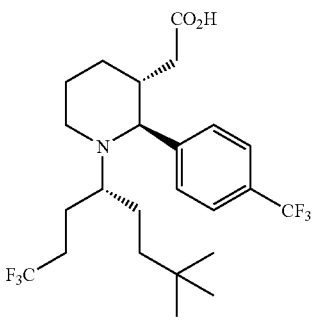 [SMILES: CC(C)(C)CC[C@H](CCC(F)(F)F)N1CCC[C@H](CC(=O)O)[C@H]1c1ccc(C(F)(F)F)cc1]

Step 1: Resolution of Intermediate 3

A solution of Intermediate 3 (1.38 g, 4.58 mmol) in DCM (50 mL) was treated with triethylamine (0.96 mL, 6.9 mmol) Boc anhydride (1.2 g, 5.5 mmol) and the resulting solution was stirred at ambient temperature for 16 hours. The reaction mixture was evaporated in vacuo and purified by flash column chromatography (0-10% ethyl acetate/hexanes). LC/MS (EIMS, M+Na)=424.1. The racemic material was purified by chiral chromatography with a Chiracel AD column (5% isopropanol/heptane) to give the two pure enantiomers. The faster eluting enantiomer was carried on to final product.

A solution of the resulting tert-butyl (2S,3R)-3-(2-methoxy-2-oxoethyl)-2-[4-(trifluoromethyl)phenyl]piperidine-1-carboxylate (2.8 g, 7.0 mmol) in DCM (50 mL) was treated with TFA (2.7 mL, 35 mmol) and stirred at ambient temperature for 16 hours. The reaction mixture was evaporated in vacuo and partitioned between saturated sodium bicarbonate solution and ethyl acetate. The organics were dried over sodium sulfate, filtered and evaporated in vacuo to give methyl {(2S,3R)-2-[4-(trifluoromethyl)phenyl]piperidin-3-yl}acetate. LC/MS (EIMS, M+H)=302.1.

Step 2: methyl {(2S,3R)-1-[((S)-4,4-dimethyl-1-(3,3,3-trifluoropropyl)pent-2-yn-1-yl]-2-[4-(trifluoromethyl)phenyl]piperidin-3-yl}acetate

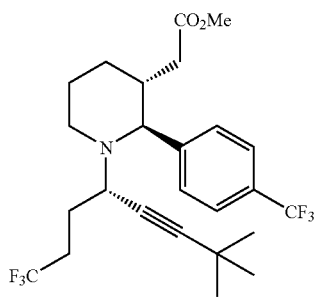 [SMILES: COC(=O)C[C@H]1CCCN([C@H](C#CC(C)(C)C)CCC(F)(F)F)[C@@H]1c1ccc(C(F)(F)F)cc1]

A solution of methyl {(2S,3R)-2-[4-(trifluoromethyl)phenyl]piperidin-3-yl}acetate (2.1 g, 7.0 mmol), 4,4,4-trifluorobutanal (1.76 g, 13.9 mmol) and gold(III) bromide (0.3 g, 0.7 mmol) in water (50 mL) was degassed with nitrogen for 1.5 hours. To this solution was added 3,3-dimethylbut-1-yne (4.3 mL, 34.8 mmol) and the reaction was sealed and heated to 70° C. for 16 hours. The reaction was partitioned between water and ethyl acetate. The organics were dried over sodium sulfate, filtered and evaporated in vacuo. Purification by flash column chromatography (3% ethyl acetate/hexanes) gave methyl {(2S,3R)-1-[(1S)-4,4-dimethyl-1-(3,3,3-trifluoropropyl)pent-2-yn-1-yl]-2-[4-(trifluoromethyl)phenyl]piperidin-3-yl}acetate as a clear oil. LC/MS (EIMS, M+H)=492.1.

Step 3: {(2S,3R)-1-[(1R)-4,4-dimethyl-1-(3,3,3-trifluoropropyl)pentyl]-2-[4-(trifluoromethyl)phenyl]piperidin-3-yl}acetic acid A solution of methyl {(2S,3R)-1-[(1S)-4,4-dimethyl-1-(3,3,3-trifluoropropyl)pent-2-yn-1-yl]-2-[4-(trifluoromethyl)phenyl]piperidin-3-yl}acetate (3.0 g, 6.1 mmol) in methanol (100 mL) was degassed with nitrogen and Raney nickel slurry was added (approx. 1.0 g of catalyst). The solution was placed on a Parr shaker under 55 psi hydrogen for 48 hours. The reaction was degassed with nitrogen and filtered through celite, washing catalyst with methylene chloride. The filtrate was evaporated in vacuo and carried into next reaction crude.

A solution of methyl {(2S,3R)-1-[(1R)-4,4-dimethyl-1-(3,3,3-trifluoropropyl)pentyl]-2-[4-(trifluoromethyl)phenyl]piperidin-3-yl}acetate (3.9 g) in methanol (50 mL) was treated with 1M potassium hydroxide in methanol (25 mL, 25.0 mmol) was heated to 60° C. for 16 hours. The reaction was treated with 25 mL 1M HCl and partitioned between water and ethyl acetate. The organics were washed with brine, dried over sodium sulfate, filtered and evaporated in vacuo. The reaction was purified by reverse phase chromatography (35-100% acetonitrile/water) to give {(2S,3R)-1-[(1R)-4,4-dimethyl-1-(3,3,3-trifluoropropyl)pentyl]-2-[4-(trifluoromethyl)phenyl]piperidin-3-yl}acetic acid as its TFA salt. This salt was taken up in ethyl acetate and treated with 10 mL concentrated HCl and stirred vigorously for 24 hours. The solution was evaporated in vacuo to give exclusively the HCl salt. $^1$H NMR (600 MHz, $CD_3OD$): δ 7.80 (bm, 4H), 4.65 (bm, 1H), 3.69 (bm, 1H), 3.22 (bm, 1H), 2.69 (bs, 2H), 2.24 (m, 1H), 2.12 (m, 4H), 2.04 (d, J=8.2 Hz, 1H), 2.01 (d, J=8.2 Hz, 1H), 1.91 (m, 3H), 1.66 (m, 1H), 1.51 (m, 1H), 1.13 (m, 1H), 0.92 (s, 9H), 0.74 (td, J=12.6, 3.8 Hz, 1H); LC/MS (EIMS, M+H)=482.1.

Assay for In Vivo Efficacy

APP-YAC transgenic mice (20-30 g; 2-6 months old) and Sprague Dawley rats (200-250 g; 8-10 weeks old) were kept on 12-hr light/dark cycle with unrestricted access to food and water. Mice and rats were fasted overnight and were then dosed orally at 10 ml/kg with test compound formulated in either imwitor: Tween-80 (50:50) or 10% Tween-80, respectively. For compound screening studies, test compounds were administered at a single dose (20 or 100 mg/kg) and blood was taken serially at 1 and 4 hrs via tail bleed from mice and terminally at 7 hrs for mice and rats via cardiac puncture. In dose response studies, compounds were given at 0.1, 3, 10, 30, and 100 mg/kg and blood was taken terminally at 7 hrs from mice and rats via cardiac puncture. Following euthanasia by $CO_2$, forebrain tissue was harvested from animals and stored at −80 degrees. For PD analysis of brain Aβ levels, soluble Aβ was extracted from hemi-forebrains by homogenization in 10 volumes of 0.2% DEA in 50 mM NaCl followed by ultracentrifugation. Levels of Aβ 42/40 were analyzed using Meso Scale technology (electrochemiluminesence) with biotinylated 4G8 capture antibody and ruthenium labeled 12F4 or G210 detection antibodies for Aβ 42 and Aβ 40, respectively. For PK analysis, blood and brain samples were processed using a protein precipitation procedure with the remaining filtrate being analyzed via LC/MS/MS to determine drug exposure levels, brain penetration, and ED50/EC50, where appropriate.

Reductions in Aβ42 levels (relative to vehicle-treated controls) for representative compounds of the invention were in the range 50-90% whereas corresponding reductions in Aβ40 levels for the same compounds were less than 20%.

The invention claimed is:

1. A compound of formula I:

I or a pharmaceutically acceptable salt thereof; wherein:
p is 0 or 1;
q is 0, 1, 2 or 3;
V represents a carbon atom whose remaining valencies are satisfied via bonding to H, $R^2$ or X-Z or to any combination thereof;
W represents a carbon atom whose remaining valencies are satisfied via bonding to H, $R^2$ or X-Z or to any combination thereof;
X represents a bond or $C(R^1)_2$ or $CH_2C(R^1)_2$;
Y represents a bond or $CH_2$ or $CH_2CH_2$;
Z represents $CO_2H$ or a tetrazole ring;
each $R^1$ independently represents H or a non-aromatic hydrocarbon group of up to 6 carbon atoms; or the two $R^1$ groups complete a $C_{3-6}$alicyclic group;
$R^2$ represents a non-aromatic hydrocarbon group of up to 6 carbon atoms;
$R^3$ and $R^4$ each represents H, or when V and W each represents a carbon atom, $R^3$ and $R^4$ may together represent a $CH_2CH_2$ bridge;
each $R^5$ independently represents halogen, $C_{1-6}$alkyl bearing 0-3 fluorine substituents, $C_{1-6}$alkoxy bearing 0-3 fluorine substituents, $C_{2-6}$alkenyl or $Si(C_{1-4}alkyl)_3$; and
$R^6$ and $R^7$ independently represent linear or branched hydrocarbon groups each containing up to 10 carbon atoms optionally bearing a substituent selected from perfluoro$C_{1-4}$alkyl, $C_{3-6}$alicyclic, hydroxy$C_{3-6}$alicyclic, OH, $C_{1-4}$alkoxy, phenyl or benzyloxy, where said $C_{1-4}$alkoxy, phenyl and benzyloxy substituents themselves bear 0-3 substituents selected from halogen, $C_{1-4}$alkyl, $C_{1-4}$alkoxy and perfluoro$C_{1-4}$alkyl.

2. A compound according to claim 1 or a pharmaceutically acceptable salt thereof wherein $R^3$ and $R^4$ both represent H.

3. A compound according to claim 1 or a pharmaceutically acceptable salt thereof wherein $(R^5)_q$ represents 2-$CF_3$, 3-$CF_3$, 4-$CF_3$, 2,4-di($CF_3$), 2-F-4-$CF_3$, 4-$OCF_3$, 4-allyl, 4-n-propyl, 4-isopropyl or 4-tert-butyl.

4. A compound according to claim 1 which is a compound of formula III:

III or a pharmaceutically acceptable salt thereof; wherein:
Y is a bond and p is 0.

5. A compound according to claim 1 which is a compound of formula IV:

IV or a pharmaceutically acceptable salt thereof; wherein:
$R^a$ represents H, halogen or $CF_3$.

6. A compound according to claim 5 or a pharmaceutically acceptable salt thereof wherein the substituted phenyl group attached to the 2-position of the piperidine ring and the CH$_2$CO$_2$H group attached in the 4-position are in the cis-configuration with respect to the piperidine ring.

7. A compound according to claim 1 or a pharmaceutically acceptable salt thereof wherein one or both of R$^6$ and R$^7$ represent unsubstituted hydrocarbon groups which may be the same or different.

8. A compound according to claim 7 or a pharmaceutically acceptable salt thereof wherein one or both of R$^6$ and R$^7$ are independently selected from methyl, ethyl, n-propyl, isopropyl, n-butyl, isobutyl, t-butyl, 3-methylbutyl, 2-ethylbutyl, 4-methylpentyl, 3,3,-dimethylbutyl, 3-methyl-1-butenyl, 3-methyl-3-butenyl, 3-methyl-3-butene-1-ynyl, 4-methyl-1-pentynyl and 3,3-dimethyl-1-butynyl.

9. A compound according to claim 1 or a pharmaceutically acceptable salt thereof wherein one or both of R$^6$ and R$^7$ bears a substituent selected from perfluoroC$_{1-4}$alkyl, C$_{3-6}$alicyclic, hydroxyC$_{3-6}$alicyclic, OH, C$_{1-4}$alkoxy, phenyl or benzyloxy, where said C$_{1-4}$alkoxy, phenyl and benzyloxy substituents themselves bear 0 to 3 substituents selected from halogen, C$_{1-4}$alkyl, C$_{1-4}$alkoxy and perfluoroC$_{1-4}$alkyl.

10. A compound according to claim 9 or a pharmaceutically acceptable salt thereof wherein one or both of R$^6$ and R$^7$ is selected from 2,2,2-trifluoroethyl, 3,3,3-trifluoropropyl, 4,4,4-trifluorobutyl, 2-phenylethyl, 3-methoxyprop-1-ynyl, cyclohexylethynyl, 1-methyl-3,3,3-trifluoropopyl, 2,2,3,3,3-pentafluoropropyl, hydroxymethyl, isopropoxymethyl, difluoromethoxymethyl, 4-benzyloxy-3-methyl-1-butynyl, 4-hydroxy-3-methyl-1-butynyl, 4-benzyloxy-3-methylbutyl, 4-hydroxy-3-methylbutyl, 2-cyclopropylethyl, 2-cyclohexylethyl, 2-(cyclohexen-1-yl)ethyl, 2-(1-hydroxycyclopentyl)ethyl, 2-(1-hydroxycyclohexyl)ethyl, 2-(3-fluorophenyl)ethyl, 2-(2,4-difluorophenyl)ethyl, 2-(3-methylphenyl)ethyl, 2-(4-t-butylphenyl)ethyl, 2-[3-(trifluoromethyl)phenyl]ethyl and 2-[4-(trifluoromethyl)phenyl]ethyl.

11. A pharmaceutical composition comprising a compound according to claim 1 or a pharmaceutically acceptable salt thereof and a pharmaceutically acceptable carrier.

* * * * *